(12) United States Patent
Wellinghoff et al.

(10) Patent No.: US 7,094,360 B2
(45) Date of Patent: Aug. 22, 2006

(54) RESIN BLENDS AND METHODS FOR MAKING SAME

(75) Inventors: Stephen T. Wellinghoff, San Antonio, TX (US); Douglas P. Hanson, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 0 days.

(21) Appl. No.: 11/010,680

(22) Filed: Dec. 13, 2004

(65) Prior Publication Data

US 2005/0189516 A1    Sep. 1, 2005

Related U.S. Application Data

(62) Division of application No. 10/190,470, filed on Jul. 5, 2002.

(60) Provisional application No. 60/303,986, filed on Jul. 9, 2001.

(51) Int. Cl.
*C09K 19/52* (2006.01)
*C09K 19/20* (2006.01)
*C08L 31/06* (2006.01)

(52) U.S. Cl. .................... 252/299.01; 252/299.64; 252/299.65; 252/299.5; 524/533; 524/559

(58) Field of Classification Search .......... 252/299.01, 252/299.64, 299.65; 433/167; 523/115–117; 264/16; 524/533, 559
See application file for complete search history.

(56) References Cited

U.S. PATENT DOCUMENTS

| | | | | |
|---|---|---|---|---|
| 4,099,856 | A | * | 7/1978 | Weissflog et al. ............ 349/23 |
| 5,676,879 | A | | 10/1997 | Heynderickx et al. |
| 5,811,504 | A | * | 9/1998 | Shiota et al. ................. 528/27 |
| 5,998,499 | A | * | 12/1999 | Klee et al. .................. 523/118 |

FOREIGN PATENT DOCUMENTS

| | | |
|---|---|---|
| GB | 2330139 A | 4/1999 |
| JP | 08-157597 | 6/1996 |
| WO | WO 98/13008 | 4/1998 |

OTHER PUBLICATIONS

Hellwig et al, Effect of the Layer Technique on the Polymerization of Two Light-Activated Composite Filling Materials, Dtsch. Zahnaerztl Z., 1991, pp. 270-273, vol. 46.

Bigg, et al.; "The Effect of Monomer Structure on the Adhesive Properties of Thermally Reversible Isocyanate Polymers"; ANTEC 2000: Conference Proceedings vol. 1—Processing; May 7, 2000-May 11, 2000; pp. 1228-1231; 58th, vol. 1; Society of Plastics Engineers, USA.

Wang, et al.; "Synthesis and Properties of Phosphorus Containing Polyester-Amides Derived from 1,4-Bis(3-aminobenzoyloxy)-2-(6-oxido-6H-dibenz<c,e><1,2>oxaphosphorin-6-yl) Phenylene"; Journal of Polymer Science: Part A: Polymer Chemistry; (1999); pp. 891-899; vol. 37; John Wiley & Sons, Inc., USA.

Kim, et al.; "Effects of Annealing on the Structure Formation in the Bulk State of Thermotropic Liquid Crystalline Polyesteramides with Bulky Side Groups"; Eur. Polym. J.; (1995) pp. 505-512; vol. 31, No. 6; Elsevier Science Ltd., UK.

Aharoni; "Dilute and Concentrated Solution Properties of Zigzag Polymers Comprising Long Rodlike Segments with Freely Rotating Joints"; Macromolecules; (1987); pp. 877-884; vol. 20, No. 4; American Chemical Society, USA.

Wan, et al.; "Relationship Between Chemical Structure and Properties for Mesogen-Jacketed Liquid Crystal Polymers"; Gaodeng Xuexiao Huaxue Xuebao; (1998); pp. 1507-1512; vol. 19, No. 9; Gaodeng Jiaoyu Chubanshe, CN; Abstract Only.

* cited by examiner

*Primary Examiner*—Shean C. Wu
(74) *Attorney, Agent, or Firm*—Paula Morris; Morris & Amatong, P.C.

(57) ABSTRACT

A resin blend and method of producing the resin blend, the resin blend comprising one or more first liquid crystal monomer at a ratio to one or more secondary monomer, said secondary monomer and said ratio being adapted to maintain said resin blend in a nematic liquid crystalline state after addition of an inorganic filler at a temperature of 20° C. for about 30 minutes or more, the resin blend having a polymerization shrinkage of 3 vol. % or less.

47 Claims, No Drawings

RESIN BLENDS AND METHODS FOR MAKING SAME

The present application is a divisional application of utility application Ser. No. 10/190,470 filed Jul. 5, 2002, which claims the benefit of U.S. Provisional Application Ser. No. 60/303,986, filed Jul. 9, 2001. The following currently pending applications, which all were filed on Jan. 23, 2002, are related to the present application: U.S. patent application Ser. Nos. 10/057,548; 10/056,121; 10/057,506. Also related is U.S. patent application Ser. No. 10/093,001, filed Mar. 7, 2002.

GOVERNMENT RIGHTS CLAUSE

The U.S. government has certain rights in this invention pursuant to grant number NIDCR 1 P01 DE11688.

FIELD OF THE INVENTION

New, efficient methods for making novel platform molecules and polymerizable mesogens are provided, as well as novel mesogens and methods of using same.

BACKGROUND OF THE INVENTION

Photocurable resins which are transparent or translucent, radioopaque, have good workability, and have good mechanical strength and stability are useful in dental applications, adhesive applications, optical applications, as composites, and in stereolithographic applications.

Low polymerization shrinkage is an important property for such resins. In dental applications, the phrase "zero polymerization shrinkage" typically means that the stresses accumulated during curing do not debond the dentin-restorative interface or fracture the tooth or restorative, which can result in marginal leakage and microbial attack of the tooth. Low polymerization shrinkage also is important to achieve accurate reproduction of photolithographic imprints and in producing optical elements.

Another advantageous property for such resins is maintenance of a liquid crystalline state during processing. For comfort in dental applications, the resin should be curable at "room temperature," defined herein as typical ambient temperature up to body temperature. Preferred curing temperatures are from about 20° C. to about 37° C. Mesogens which have been found to polymerize in a relatively stable manner at such temperatures are bis 1,4[4'-(6'-methacryloxyhexyloxy)benzoyloxy]t-butylphenylene mesogens and their structural derivatives. These mesogens have the following general structure:

Unfortunately known synthetic methods for producing these mesogens are costly and have relatively low yields. As a result, the mesogens have enjoyed limited commercial use.

Less costly and simple synthetic methods are needed to produce these mesogens and/or to produce new mesogens that exhibit suitable viscosity for ease in handling, minimal polymerization shrinkage, and relatively high transition temperatures ("$T_{n \rightarrow isotropic}$").

SUMMARY OF THE INVENTION

In one embodiment, the present application provides a resin blend comprising:

one or more first liquid crystal monomer at a ratio to one or more secondary monomer, said secondary monomer and said ratio being adapted to maintain said resin blend in a nematic liquid crystalline state after addition of inorganic filler at a temperature of 20° C. for about 30 minutes or more, the resin blend having a polymerization shrinkage of 3 vol. % or less, the primary liquid crystal monomer having the following general structure:

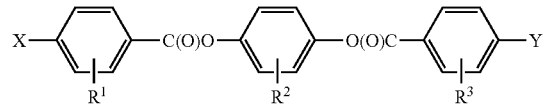

wherein X and Y comprise polymerizable groups;

$R^2$ is a bulky organic group having a bulk greater than $R_1$ and $R_3$, said bulk being adapted to provide sufficient steric hindrance to achieve a nematic state at room temperature while suppressing crystallinity of liquid crystal monomers made using the mesogens at room temperature; and, $R^1$ and $R^3$ are selected from groups less bulky than $R^2$;

said secondary monomer comprising one or more mesogens having the following general structure:

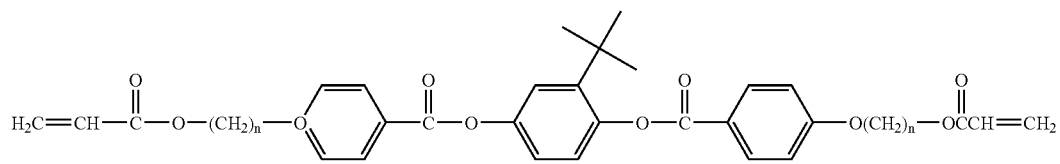

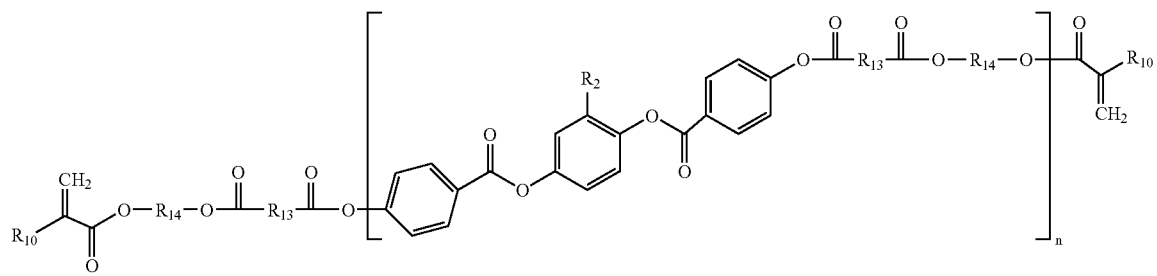

wherein:
 n is from about 2 to about 5;
 $R^2$ is a bulky organic group;
 $R^{10}$ independently is selected from the group consisting of hydrogen and methyl groups;
 $R^{14}$ independently is selected from the group consisting of substituted and unsubstituted alkyl groups having from about 2 to about 6 carbon atoms, provided that said substituted alkyl groups consist essentially of one or fewer methyl substituents;
 $R^{13}$ independently is selected from the group consisting of alkylene groups having from about 2 to about 12 carbon atoms.

In another embodiment, the application provides a method for producing a resin blend comprising
 producing a mixture comprising a quantity of primary polymerizable mesogen and an amount of one or more secondary polymerizable mesogen selected from the group consisting of mesogenic dimers and polymerizable elongated diphenolic platform molecules comprising four phenylene rings or more, wherein said resin blend has a curing temperature ($T_c$) of about 40° C. or less and, upon curing, exhibits a polymerization shrinkage of about 3 vol % change or less,
 said primary polymerizable mesogen having the following general structure:

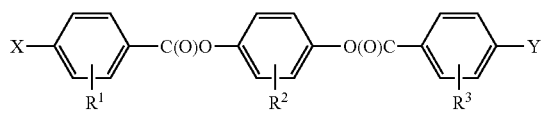

wherein X and Y comprise polymerizable groups;
 $R^2$ is a bulky organic group having a bulk greater than $R_1$ and $R_3$, said bulk being adapted to provide sufficient steric hindrance to achieve a nematic state at room temperature while suppressing crystallinity of liquid crystal monomers made using the mesogens at room temperature; and,
 $R^1$ and $R^3$ are selected from groups less bulky than $R^2$.

DETAILED DESCRIPTION OF THE INVENTION

The application provides novel platform molecules, novel polymerizable mesogens, novel methods for using the platform molecules, and novel intermediates and synthetic pathways for making the platform molecules and polymerizable mesogens.

The Mesogens
 The mesogens of the present application have the following general structure:

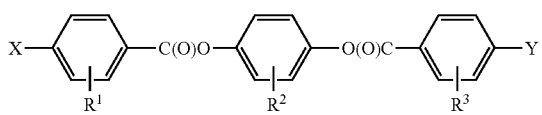

wherein X and Y are selected from the group consisting of terminal functionalities and polymerizable groups. In platform molecules, X and Y are terminal functionalities. In polymerizable mesogens, X and Y are polymerizable groups. Terminal functionalities and polymerizable groups are further defined below; and,
 $R^2$ is a "bulky organic group," defined herein as an organic group having a bulk greater than $R_1$ and $R_3$, said bulk being adapted to provide sufficient steric hindrance to achieve a nematic state at room temperature while suppressing crystallinity of liquid crystal monomers made using the mesogens at room temperature. The result is effective rheology and workability at room temperature. Suitable $R^2$ groups generate asymmetry in the packing of the molecules, and include, but are not necessarily limited to methyl groups, t-butyl groups, isopropyl groups, phenyl groups, and secondary butyl groups. Most preferred $R^2$ groups are t-butyl groups; and
 $R^1$ and $R^3$ are selected from groups less bulky than $R^2$, preferably selected from the group consisting of hydrogen atoms and methyl groups.

As used herein, the phrase "terminal functionalities" refers to X and Y where the referenced molecules are platform molecules. "Terminal functionalities" are defined as functionalities that readily react with "polymerizable groups" to form reactive ends. Suitable terminal functionalities independently are selected from the group consisting of hydroxyl groups, amino groups, sulfhydryl groups, halogen atoms, and alkoxy groups. Most preferred terminal functionalities are hydroxyl groups.

Where the mesogen is a polymerizable mesogen, X and/or Y are "polymerizable groups," defined as groups that may be polymerized either by free radical polymerization or by nucleophilic addition, including but not necessarily limited to Michael addition.

Michael addition requires the addition of a nucleophile and an electron deficient alkene. Groups suitable for polymerization by Michael addition include but are not necessarily limited to the examples found in A. Michael, *J. Prakt. Chem.* [2] 35, 349 (1887); R. Connor and W. R. McClelland, *J. Org Chem.*, 3, 570 (1938); and C. R. Hauser, M. T.

Tetenbaum, *J. Org. Chem.*, 23, 1146 (1959), all of which are incorporated by reference herein.

Examples of suitable polymerizable groups include, but are not necessarily limited to groups comprising terminal polymerizable unsaturated carbon-carbon bond(s) and epoxy group(s). Where the polymerizable group is a terminal alkenyl ester group, the carbonyl of the terminal alkenyl ester group is bonded to the platform molecule via a connecting group. Preferred connecting groups are selected from the group consisting of:

- an alkyleneoxy group comprising an oxygen atom and an alkylene moiety having from about 0 to about 1 methyl substituents and having from about 2 to about 12 carbon atoms, preferably about 6 carbon atoms, wherein said carbonyl of said terminal alkenyl ester group is bonded to said alkylene moiety and said oxygen is bonded to said platform molecule; and,
- an alkylene group or a methyl substituted alkylene group having from about 2 to about 6 carbon atoms, preferably about 2 carbon atoms, bonded to first carbonyl of a diester of comprising an alkylene group having from about 2 to about 12 carbon atoms, said diester comprising a second carbonyl group bonded to said platform molecule.

Applicant here claims novel and non-obvious combinations of polymerizable groups on the mesogens other than bis-acryloyloxy alkyloxy and bismethacryloyloxy alkyloxy polymerizable mesogens and novel polymerizable groups.

A preferred embodiment comprises monomers having the following general structure:

achieve a nematic state at room temperature while suppressing crystallinity of liquid crystal monomers made using the mesogens at room temperature;

$R^{10}$ independently is selected from the group consisting of hydrogen and methyl groups;

$R^{14}$ independently is selected from the group consisting of substituted and unsubstituted alkyl groups having from about 2 to about 6 carbon atoms, provided that said substituted alkyl groups consist essentially of one or fewer methyl substituents;

$R^{13}$ independently is selected from the group consisting of alkylene groups having from about 2 to about 12 carbon atoms.

Suitable $R^2$ groups generate asymmetry in the packing of the molecules, and include, but are not necessarily limited to methyl groups, t-butyl groups, isopropyl groups, phenyl groups, and secondary butyl groups. Most preferred $R^2$ groups are t-butyl groups. Increasing the number of structural variations decreases the potential of any one component to crystallize at the polymerization temperature.

In a preferred embodiment, $R^{14}$ has the following general structure:

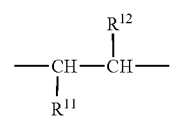

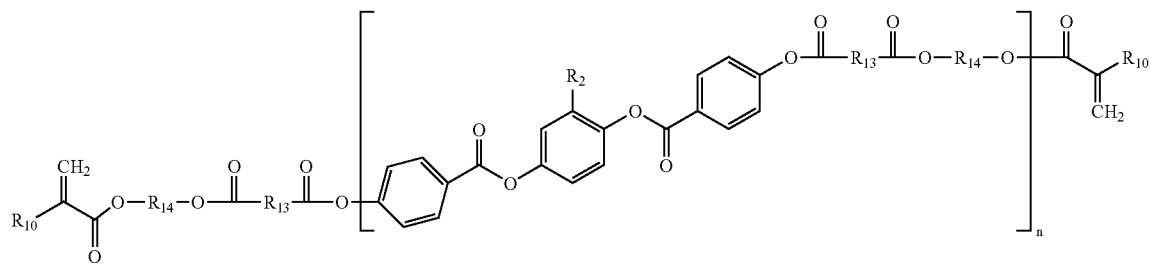

wherein:

n is 1;

$R^2$ is a bulky organic group defined herein as an organic group having a bulk greater than $R_1$ and $R_3$, said bulk being adapted to provide sufficient steric hindrance to wherein $R^{11}$ and $R^{12}$ independently are selected from the group consisting of hydrogen and methyl groups, provided that only one of $R^{11}$ and only one of $R^{12}$ is a methyl group. In this embodiment, the monomers have the following structure:

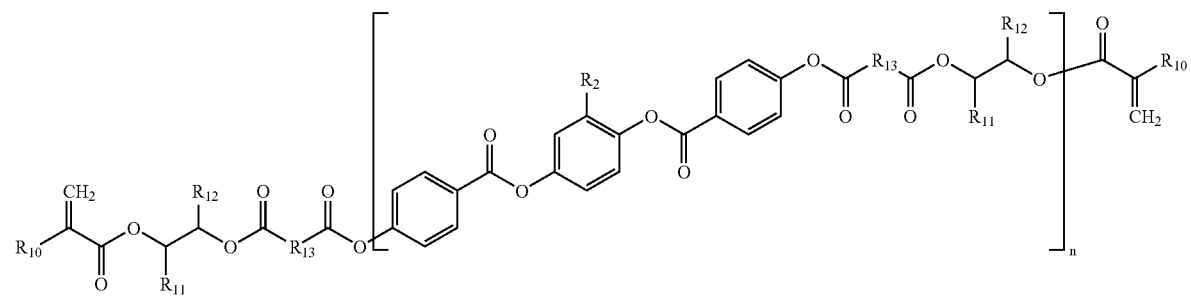

The foregoing monomers are sometimes called oligo {[α,ω-dialkanoyl]-co-[(bis-1,4-oxybenzoyloxy)-1',4'-(2'-R²-phenylene)]-α'-{X}, wherein the X-terminal group is selected from the group consisting of oxyalkyl(meth)acrylate groups, (meth)acrylate groups, and carbonylalkanoyl oxyalkyl(meth)acrylate groups.

Other preferred polymerizable mesogens are-bis 1,4[4'-(6'-(R,R⁴)-oxy-A-oxy)benzoyloxy]R²-phenylene mesogens. These mesogens have the following general structure:

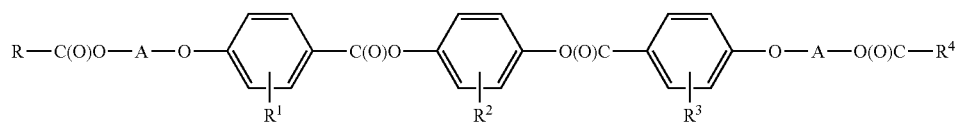

This structure is similar to the structure of the platform molecules except that X and Y are replaced by polymerizable groups wherein:

A is selected from the group consisting of alkyl groups and methyl-substituted alkyl groups having from about 2 to about 12 carbon atoms, preferably having from about 2 to about 9 carbon atoms, more preferably having from about 2 to about 6 carbon atoms, and most preferably having about 6 carbon atoms; and R and R⁴ are polymerizable groups, including but not necessarily limited to nucleophiles and groups comprising at least one electron deficient alkene. Suitable nucleophiles include, but are not necessarily limited to ester groups, organic acid groups, amine groups, hydroxyl groups, and sulfhydryl groups. More preferred polymerizable groups comprise electron deficient alkenes. Preferred electron deficient alkenes independently are selected from the group consisting of substituted and unsubstituted alkenyl ester groups comprising a polymerizable unsaturated carbon-carbon bond, wherein said alkenyl group has from about 2 to about 12 carbon atoms. Preferred alkenyl esters are acryloyl groups and methacryloyl groups, said substituted alkenyl ester groups comprising at least one halogen atom selected from the group consisting of chorine atoms, bromine atoms, and iodine atoms. Again, because asymmetry suppresses crystallinity while maintaining a nematic state, it is preferred for X and Y to be different groups. One end of a polymerizable mesogen also may comprise a bridging agent, as discussed below.

In a preferred embodiment, R² is a t-butyl group, A is a hexyl group, and one of R and R⁴ is selected from the group consisting of an acryl group and a methacryl group.

In a preferred embodiment, a proportion of X and/or Y (or R and/or R⁴) comprises a crystallization retardant. A "crystallization retardant" is defined as a substituent that retards crystallization of the monomers without suppressing the $T_{n \rightarrow isotropic}$ (the nematic to isotropic transition temperature). The proportion of X and/or Y (or R and/or R⁴) that comprises a crystallization retardant preferably is sufficient to suppress crystallinity of the mesogenic material, particularly at room temperature for dental applications, and to maintain flowability of the mesogenic material under the particular processing conditions. Suitable crystallization retardants include, but are not necessarily limited to halogen atoms. Exemplary halogen atoms are chlorine, bromine, and iodine, preferably chlorine. Typically, the proportion of the crystallization retardant required is about 3–50 mole %, more preferably 10–15 mole %, and most preferably about 14 mole % or less.

Depending on the sample preparation, the volumetric photopolymerization shrinkage of these materials at room temperature varies between 0.9–1.7%, which is a factor of 6-4 X improvement over commercially available blends containing 2,2-bis[p-(2'-hydroxy-3'-methacryloxypropoxy)phenylene]propane ("bis-GMA"). Preferable, the volumetric polymerization shrinkage is about 3 vol. % change or less, more preferably about 2 vol. % change or less.

Mesomers of higher temperature nematic stability are "mesogenic dimers," formed by reacting X and Y with opposite ends of a bridging agent. Examples of suitable bridging agents include, but are not necessarily limited to dicarboxylic acids (preferably α,ω-carboxylic acids) having from about 4 to about 12 carbon atoms, preferably from about 6 to about 10 carbon atoms, and oligodialkylsiloxanes preferably comprising alkyl groups having from about 1 to about 3 carbon atoms, most preferably methyl groups.

New Synthetic Pathways to Make the Mesogens

In the past, polymerizable mesogens having the foregoing structure were synthesized by a multistep process ("Scheme 1"), as shown below:

Scheme 1.

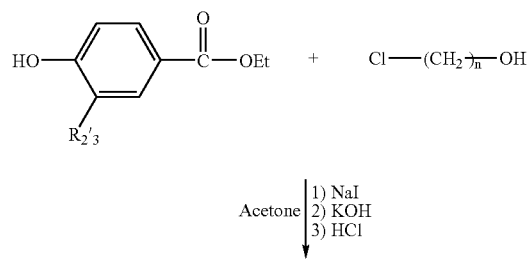

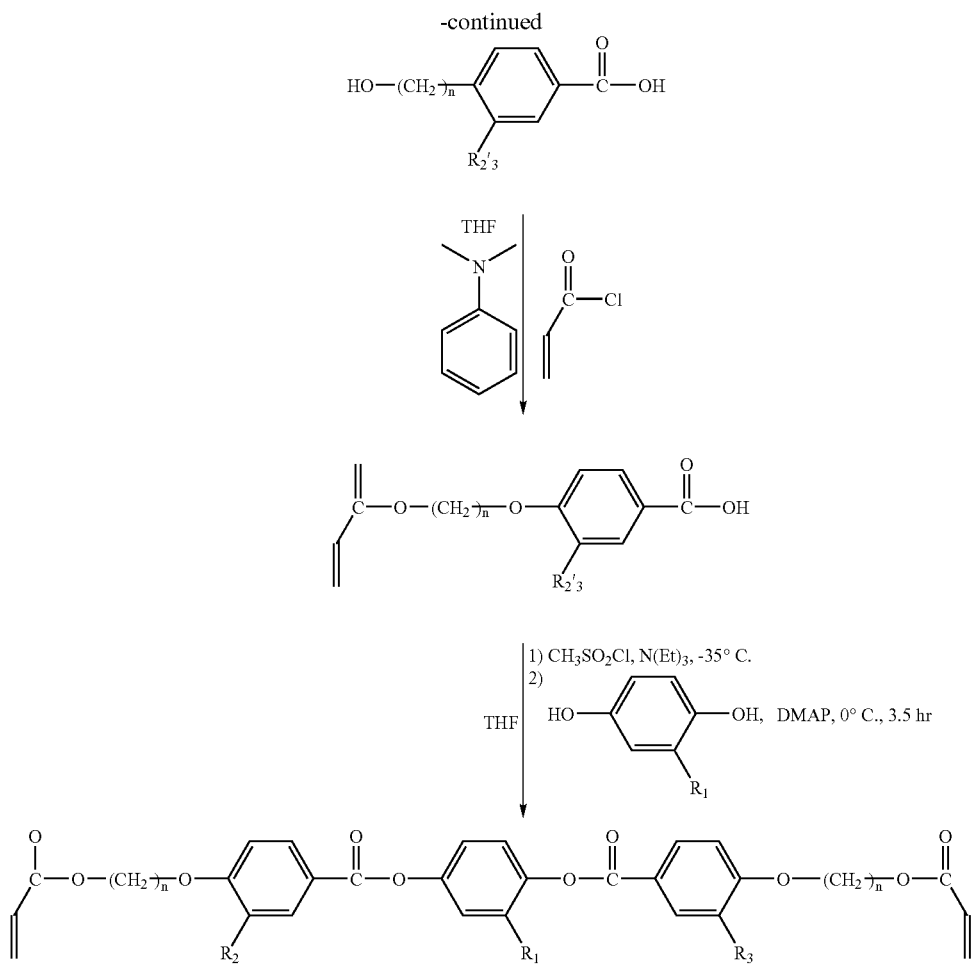

In Scheme 1, molecular ends containing the outer aromatic groups and the alkyl groups were produced first and then coupled to the central aromatic group by diaryl ester bonds. Specifically, the alkali phenoxide salt of p-hydroxybenzoic acid-ethyl ester ($0.70/mole) nucleophile attacked the 6-hydroxy 1-chloro hexane with the aid of iodide catalyst to produce the 6-hydroxyhexyloxybenzoic acid (after hydrolysis of the ethyl ester) by a procedure that yielded at best 70% product. Although rather straightforward, the commercial potential of this synthesis has been limited by the use of the 6-hydroxy 1-chlorohexane, whose minimal bulk price for $n \geq 4$ is $100/kg ($13.62/mole, n=6). The reaction is run in acetone over several days and requires significant workup. The reaction also produces only about a 40% overall yield, at best, and requires column separation to separate monosubstituted from disubstituted material The present application provides new synthetic pathways for synthesizing platform molecules and polymerizable mesogens. In one aspect, the application provides a method that uses relatively low cost materials to synthesize a central aromatic component comprising end groups that are easily reacted with the desired polymerizable groups. The methods are qualitative, produce high yields, the products are easily purified (preferably by crystallization), and many of the products are more stable than bisalkenes, which must be stabilized against polymerization. In another aspect, the application provides a novel, efficient, and economic process to form polymerizable ends which are coupled with bis, 1,4[4'-hydroxybenzoyloxy]-$R^2$-phenylene to form monomers, dimers, and trimers, which are preferably are separable by solvent extraction.

Brief Summary of the Processes

According to the present application, functionalities on a phenylene ring at para-positions (preferably hydroxyl groups) form ester linkages with one of two functionalities in para-positions on two other phenylene rings. The result is three-ring platform molecules having terminal functionalities. One or both of the terminal functionalities may be coupled with polymerizable groups, preferably a nucleophile and/or an electron deficient alkene-containing group, to produce polymerizable mesogens.

Preparation of Molecular Ends and Coupling to Central Aromatic Group

In a first embodiment of the application (Scheme 2), the molecular ends of the mesogen (outer aromatic and alkyl groups) are prepared and coupled to the central aromatic group by diaryl ester bonds. This synthetic pathway is illustrated and described in detail below:

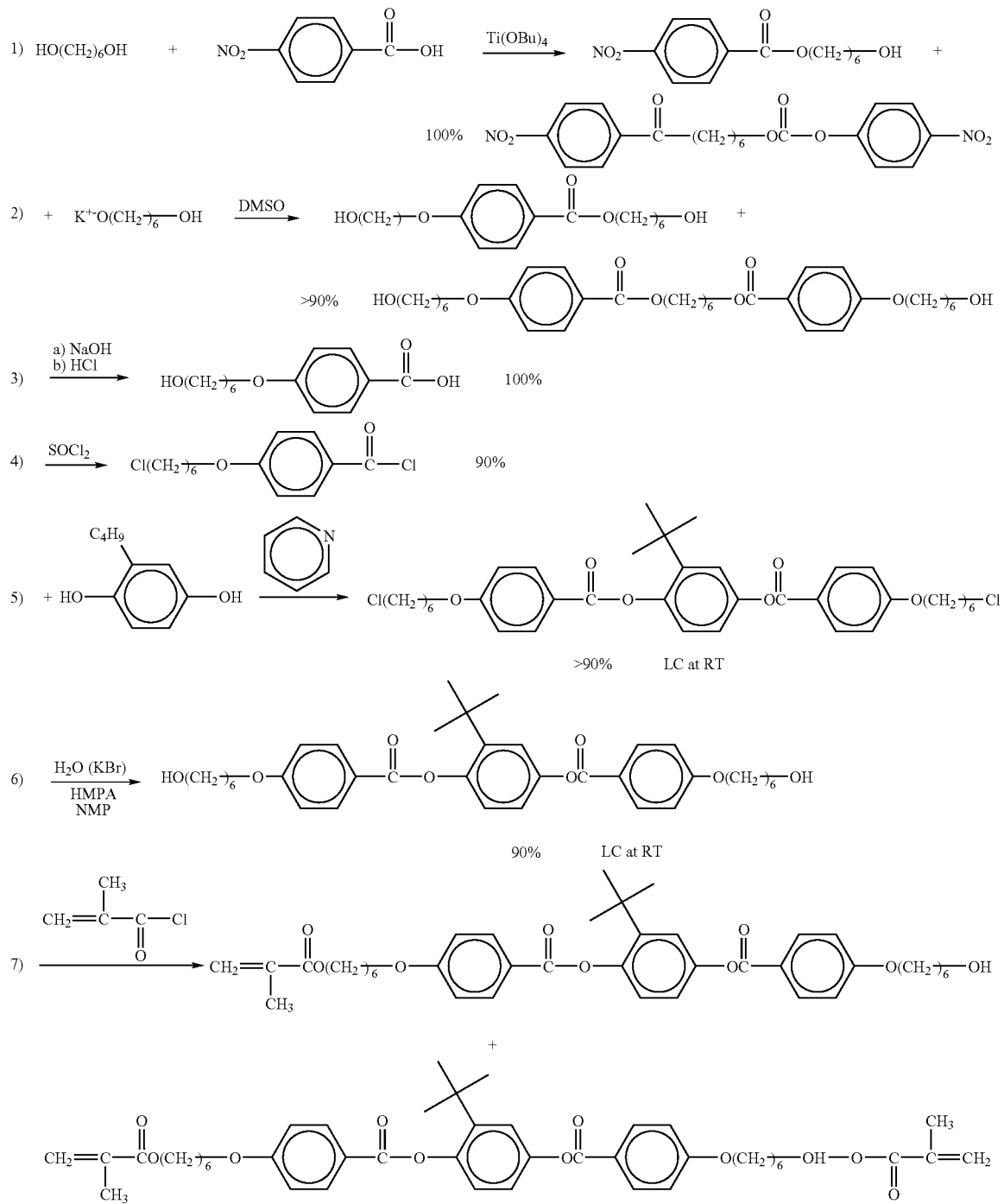

Scheme 2.

Exemplary "platform molecules" are illustrated in (6), above.

To summarize Scheme 2, bis 1,4[4"-(6'-chloroalkyloxy) benzoyloxy]R²-phenylene, preferably bis 1,4[4"-(6'-chlorohexyloxy) benzoyloxy]t-butylphenylene, is converted to the analogous bis e)-hydroxy or co-hydroxy chloro compound. The hydroxy-compound (the platform molecule) may be terminated with one or more polymerizable groups. Preferred polymerizable groups are nucleophilic and electron deficient groups, most preferably independently selected from the group consisting of acryloyl groups, methacryloyl groups, and cinnamoyl groups.

More particularly:

(1) 4-nitrobenzoic acid is dissolved in an excess of the desired 1,6-dihydroalkane, preferably 1,6-dihydroxyhexane, in the presence of a suitable esterification catalyst. Suitable catalysts include, but are not necessarily limited to titanium alkoxides, tin alkoxides, sulfonic acid, and the like. A preferred catalyst is Ti(OBu)$_4$. The dissolution occurs at atmospheric pressure at a temperature of from about 120° C. to about 140° C., with stirring. If excess alcohol is used, the majority product is the 6-hydroxyalkyl ester of 4-nitrobenzoic acid plus some bis 1,6-(4-nitrobenzoyloxy) alkane, preferably 1,6-(4-nitrobenzoyloxy) hexane. The byproduct water is removed using suitable means, preferably under vacuum during the course of the reaction.

(2) One or more suitable solvents are added to the reaction mixture, along with alkali salts of diols. Suitable solvents include, but are not necessarily limited to aprotic solvents in which nucleophilic attack is preferred. Examples include, but are not necessarily limited to dimethyl sulfoxide (DMSO), dimethyl formamide (DMF), dimethyl acetamide (DMAC), hexamethyl phosphonamide (HMPA). A preferred solvent is dimethylsulfoxide (DMSO), which is environmentally safe and relatively inexpensive ($2.00/kg). Suitable salts comprise cations effective to displace hydrogen and to produce the mono-cation salt of the alkanediol, preferably the nucleophilic monosodium salt of hexanediol, in the presence of excess alkyldiol, preferably hexanediol. Preferred salts include, but are not necessarily limited to NaH ($0.57/mole) or KOBu$^t$. The salt of the alkane diol, preferably hexane diol, then displaces the activated nitro group to produce 4-(1-hydroxyalkyloxy)benzoic acid (1-hydroxyalkyl ester) and some of the dimeric compound. A preferred product is 4-(1-hydroxyhexyloxy)benzoic acid (1-hydroxyhexyl ester) and some of the dimeric compound. See N. Kornblum et al., J. Org. Chem., 41(9), 1560 (1976), incorporated herein by reference (nucleophilic displacement of nitro-group).

(3) The mixture from (2) is diluted with an aqueous base and heated to completely cleave the aryl-alkyl ester to produce the desired 4-(6'-hydroxyakyloxy)benzoic acid by precipitation subsequent to acidification. Suitable aqueous bases include, but are not necessarily limited to inorganic bases, a preferred base being aqueous sodium hydroxide. Suitable acids include, but are not necessarily limited to inorganic acids, a preferred acid being hydrochloric acid. In a preferred embodiment, 4-(1-hydroxyhexyloxy)benzoic acid (1-hydroxyhexyl ester) is diluted with aqueous sodium hydroxide and then acidified using hydrochloric acid to produce 4-(6'-hydroxyhexyloxy)benzoic acid. The supernatant contains sodium chloride and nitrite, which can be removed and recovered by vacuum evaporation of the solvent. In a preferred embodiment, the solvents evaporated are DMSO, hexanediol and water, which may be discarded. DMSO and hexanediol can be recovered from the water phase by known distillation procedures.

(4) In a preferred embodiment, for small scale procedures, a quantitative conversion of the 4-(6'-hydroxyalkyloxyben-zoic acid to 4-(6'-chloroalkyloxy)benzoyl chloride is accomplished by mixing with thionyl chloride diluted in a suitable solvent, preferably toluene, in the presence of pyridine base. In a preferred embodiment, 4-(6'-hydroxyhexyloxy)benzoic acid is converted to 4-(6'-chlorohexyloxy)benzoyl chloride in this manner. On a larger scale, the foregoing reaction is implemented with simple addition of SOCl$_2$ and venting of the byproduct SO$_2$ and HCl.

(5) The highly reactive 4-(6'-chloroakyl)benzoyl chloride is coupled to a hydroquinone bearing the desired bulky group, R$^2$. In a preferred embodiment, 4-(6'-chlorohexyl) benzoyl chloride is mixed at room temperature with t-butyl hydroquinone in ether with pyridine, used as catalyst and as a base to take up released HCl, to form bis 1,4[4"-(6'-hydroxyhexyloxy) benzoyloxy]t-butylphenylene. The reaction is quantitative and produces a high yield of the desired product. In addition, the bis 1,4[4"-(6'-chloroalkloxy) benzoyloxy]R$^2$-phenylene, preferably bis 1,4[4"-(6'-chlorohexyloxy)benzoyloxy]t-butyl phenylene, is easily purified from the reaction mixture by crystallization. In addition, the bischloro compound is stable and need not be stabilized against polymerization (as must bis-alkene compounds).

(6) The bischloro compound is hydrolyzed to the platform molecule, preferably bis 1,4[4"-(6'-chlorohexyloxy)benzoyloxy]t-butylphenylene, by simple heating in an aprotic solvent in the presence of water [R. O. Hutchins and I. M. Taffer, J.Org. Chem, 48, 1360 (1983)]. Again, the reaction is quantitative with the product being purified by recrystallization. The reaction can be stopped at intermediate times to produce any desired mixture of monofunctional and difunctional alcohol molecules. In addition, the chloro-terminated molecules can be converted to the more reactive iodo-terminated species by simple exchange with NaI in acetone.

(7) The dialcohol or mixed alcohol/alkyl chloride is easily reacted with one or more polymerizable groups, preferably Michael addition reactants. In a preferred embodiment, one or more of the dialcohol ends is reacted with alkenyl chlorides to form reactive alkenyl esters, which can have any ratio of alkenyl ester, halide, or alcohol termini. The ratio can be adjusted to adjust the crosslink density and the liquid crystal transition temperatures.

In another embodiment, 4-methoxy benzoyl chloride is reacted with a hydroquinone substituted with a desired R$^2$ group, preferably a t-butyl group, to produce the bis 1,4[4-methoxybenzoyloxy]t-butylphenylene. The methyl group of this compound is selectively cleaved with thioethane and aluminum chloride to produce bis 1,4[4'-hydroxybenzoyloxy]t-butylphenylene. See M. Node et al., J. Org. Chem., 45, 4275 (1980)] (FIG. 7a), incorporated herein by reference. The same procedure can be used to form diphenols with methyl, n-alkyl, halogen, and other groups substituted on the central aromatic ring.

Since methyl ether cleavage is always in competition with diaryl ester cleavage in this reaction and Friedel-Kraft substitution of the aromatic rings, the desired compounds can be produced only when reaction temperatures and times and thiol-aluminum chloride-solvent compositions are adjusted into narrow ranges. Quantitative yields are obtained when the diphenol crystallizes directly from the reaction mixture, effectively removing the molecule from further reaction that would form side products:

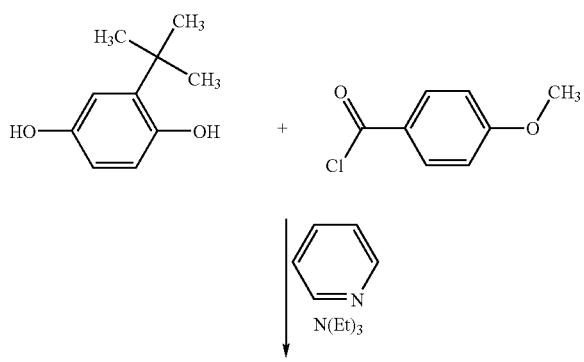

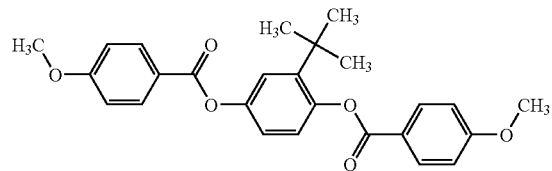

m.p. = 138–140° C.
Yield = 90%

| AlCl₃
| CH₃CH₂SH
↓

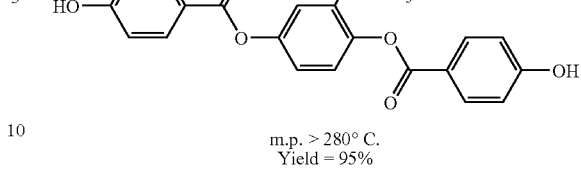

m.p. > 280° C.
Yield = 95%

The diphenolic platform mesogens can be lengthened by reacting additional 4-methoxy benzoyl chloride with bis 1,4[4'-methoxybenzoyloxy]t-butylphenylene to produce the dimethoxy compound with four or five aromatic rings, depending upon the reactant ratios. Cleavage with Lewis acid and thiol produces the respective elongated diphenolic platform molecules:

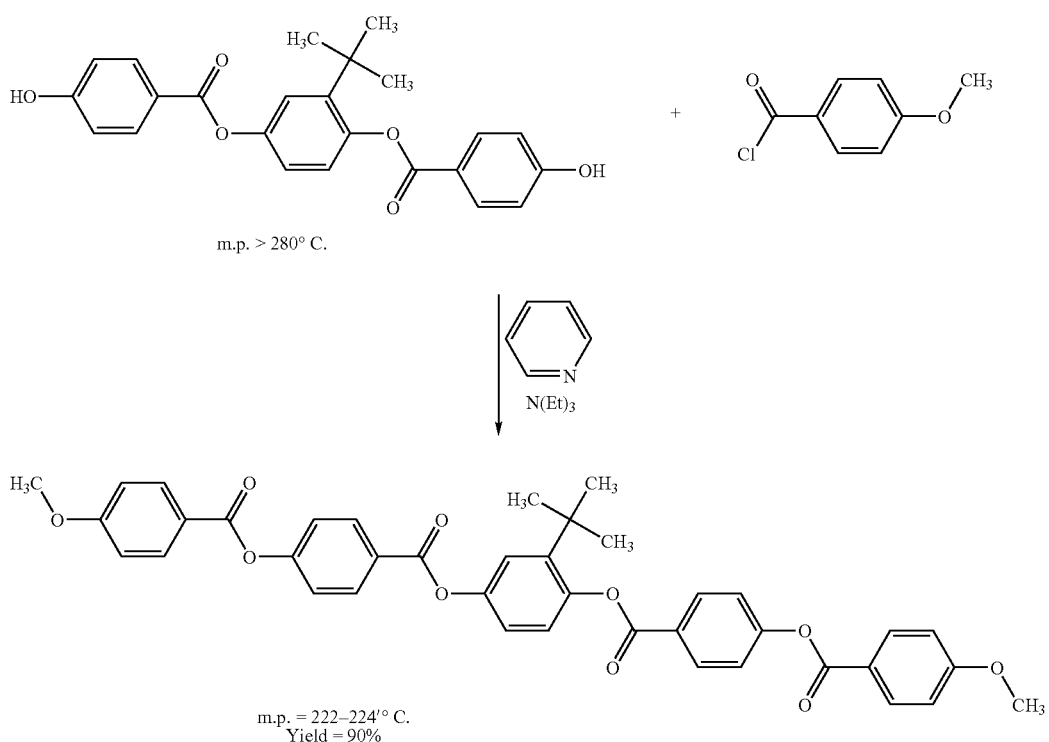

m.p. > 280° C.

| pyridine
| N(Et)₃
↓ m.p. = 222–224'° C.
Yield = 90%

| AlCl₃
| CH₃CH₂SH
↓

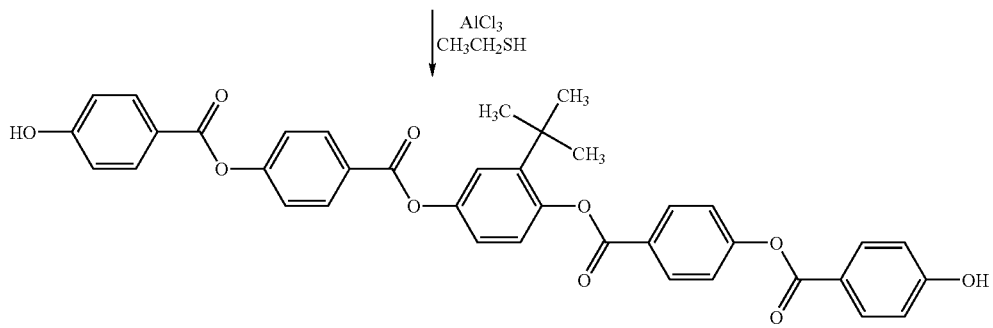

The phenolic end group(s) are esterified by acyl chlorides, thus providing a route to polymerizable mesogens. For example, reaction of CO[H,TB,H](OH)$_2$ with methacryloyl chloride formed the monoester which was coupled to bifunctional sebacoyl chloride to form an alkyl diester linked, methacrylate terminated liquid crystalline monomer, {CO[H,TB,H](MeAcry)(O)}$_2$ (seb) with T$_{n\rightarrow 1}$ of 145° C. and a T$_g$ of 25° C. This monomer had no tendency to crystallize since the synthesis yielded three different isomers with differing mutual orientation of t-butyl groups. The material is highly viscous, however, making processing close to room temperature, and thus T$_g$, somewhat inconvenient.

Production of Molecular Ends and Coupling with bis, 1,4[4'-hydroxybenzoyloxy]-R$^2$-phenylene Another method synthesizes the monomers, described above, having the following general structure:

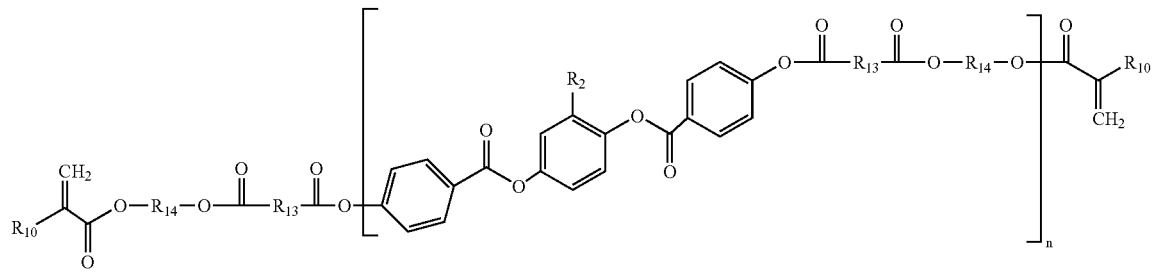

In this synthesis, a difunctional acyl chloride having from about 2 to about 12 carbon atoms, such as adipoyl, sebacoyl, or other dicarboxylic acyl chlorides, or a mixture of dicarboxylic acyl chlorides, is dissolved in a solvent, preferably in the presence of a hindered amine. Suitable solvents include, but are not necessarily limited to alkyl halides, ethers, and mixtures thereof. Suitable alkyl halides have from about 1 to about 2 carbon atoms and include, but are not necessarily limited to methylene chloride and dichloroethane. Suitable ethers include, but are not necessarily limited to cyclic ethers, such as THF. Suitable hindered amines include but are not necessarily limited to aromatic substituted amines, preferably di- or tri-aromatic substituted amines, such as, tribenzyl amine. The presence of a hindered amine is useful to prevent precipitation of oligomeric complexes of the difunctional acyl chloride.

Preferably, a cosolvent or catalyst (hereinafter "cosolvent") also is present. Suitable cosolvents are heterocyclic compounds comprising a ring structure having from about 5 to about 6 members, and comprising nitrogen as a member of said ring structure. Examples of suitable cosolvents include, but are not necessary limited to pyridine and 4-dimethylaminopyridine. A preferred cosolvent is pyridine.

Hydroxyalkyl groups comprising a suitable polymerizable moiety are added to produce a mixture comprising monoester, diester, and unreacted dicarboxylic acyl chloride. Preferred hydroxyalkyl groups include, but are not necessarily limited to hydroxyalkylacrylates and/or hydroxyalkyl methacrylates comprising an alkyl groups having from about 2 to about 12 carbon atoms, preferably from about 2 to about 9 carbon atoms, more preferably from about 2 to about 6 carbon atoms, and most preferably from about 2 to about 3 carbon atoms. Most preferred hydroxyalkyl acrylates and hydroxyalkyl methacrylates are selected from the group consisting of hydroxyethyl methacrylate, hydroxypropyl methacrylate, hydroxyethyl acrylate, hydroxypropyl acrylate, and mixtures thereof.

If one or more epoxy functional end is desired, 3-hydroxy-1,2-epoxypropane(glycidol) or 2-methyl-3-hydroxy-1,2-epoxypropane(2-methyl glycidol) is substituted for hydroxyethylmethacrylate or hydroxypropylmethacrylate in the reaction with the difunctional acyl chloride.

The success of this synthesis is not noticeably dependent on the relative sequence of addition of the reactive components. The ratio of mono-esters and diesters may be controlled by controlling the stoichiometry of the hydroxyalkyl acrylate to diacid chloride.

In a final synthetic step, to the solution is added bis 1,4[4'-hydroxybenzoyloxy]-R$^2$-phenylene, preferably bis 1,4[4'-hydroxybenzoyloxy]t-butylphenylene, most preferably a mixture of bis 1,4[4'-hydroxybenzoyloxy]-R$^2$-phenylene wherein R$^2$ is at least two bulky organic groups. Suitable bulky organic groups were defined previously. Examples of suitable groups are selected from the group consisting of methyl groups, t-butyl groups, isopropyl groups, phenyl groups, and secondary butyl groups, and combinations thereof. Most preferred bulky organic groups are t-butyl groups and methyl groups. The bis 1,4[4'-hydroxybenzoyloxy]-R$^2$-phenylene(s) are added to the above reaction mixture either in solution or as a solid in the presence of pyridine or dimethylaminopyridine or other catalyst(s). Depending on the initial ratio of hydroxyester to diacyl chloride, the reaction produces varying mixtures of alkene functionalized monomer, dimer, trimer, etc., and unreacted diester of hydroxy alkyl acrylate and diacyl chloride.

Solvent and amine chlorides are then removed from the mixture. Unreacted diester of hydroxy alkyl acrylate and dicarboxylic acyl chloride are removed by continuous extraction by an alkane (hexane, isopentane, etc.). To the resulting resin is added a quantity of a thermal initiator or photoinitiator, and the resin is polymerized thermally or by photopolymerization.

Alternatively, the mixture is separated into its respective components by selective solvent extraction. For example, referring the following general structure:

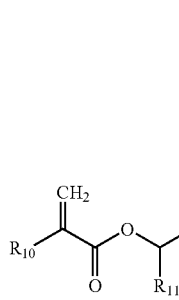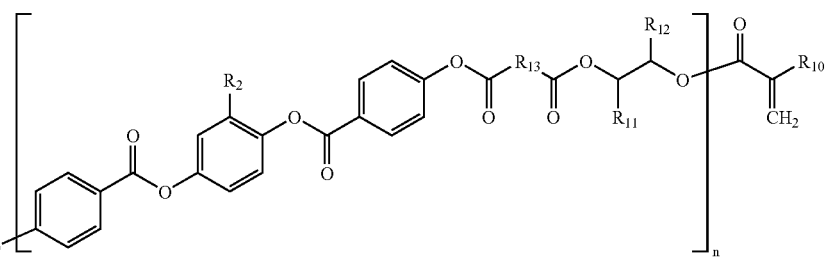

monomeric structures, wherein n is 1, are soluble in alkanols, such as isopropyl alcohol and methanol. Dimers (n is 2) are soluble in ethers, such as diethyl ether, but are relatively insoluble in low molecular weight alcohols. Higher oligomers, such as trimers (n is 3), are relatively insoluble.

A strategy to produce blends with the desired properties is to continuously extract monomer from the blend until the required monomer/oligomer ratio is reached. The blends of various syntheses may be then further blended or separated into their various functional "mers" by the process described above and then blended.

Formation of Dimers

Preferred dimeric (M2) and polymeric (LCP) derivatives of C6[H,TB,H]type mesogenic cores are much more unlikely to crystallize [S. Lee et al., Macromol., 27(14), 3955 (1994)] (Table 3), incorporated herein by reference. In addition, blends of LCP (and, most likely, M2) with M1, (C6[H,TB,H](Me)$_2$, generate a phase diagram with isotropic, isotropic+nematic and finally, at the lowest temperatures, a nematic phase. Adding polymer to the monomer substantially increases $T_{n \to n+1}$.

Briefly, in order to make the dimer molecule, a second mesogenic, platform molecule, 1,4[4'-hydroxybenzoyloxy] t-butylphenylene, CO[H,TB,H](OH)$_2$, is synthesized by coupling p-anisoyl chloride with t-butyl hydroquinone and then cleaving the methoxy end groups with ethanethiol ($4/kg) and aluminum chloride ($5/kg, $0.66/mole). This molecule can be further extended by reaction with p-anisoyl chloride ($30/kg, $5.10/mole) and the same methoxy cleavage reaction. Fully aromatic diphenol terminated mesogens of any length can be thus produced.

Reaction of CO[H,TB,H](OH)$_2$ with a less than stoichiometric amount of methacryloyl chloride forms the monoester and diester. The monoester and diester are washed away from the diphenol starting material with methylene chloride and the monoester is separated from the diester as an insoluble solid by diluting the methylene chloride solution into hexane.

The monoester can be coupled to bifunctional sebacoyl chloride ($25/kg, $6/mole) to form an alkyl diester linked, methacrylate terminated liquid crystalline monomer, {CO[H,TB,H](MeAcry)(O)}$_2$ (seb) with $T_{n \to 1}$ of 145° C. and a $T_g$ of 25° C. This monomer has no tendency to crystallize since the synthesis yields three different isomers with differing mutual orientation of t-butyl groups. However, processing close to room temperature, and thus $T_g$, is inconvenient because of the high viscosity of the material.

The following is a ChemSketch 4 rendition of the minimum energy conformation of {CO[H,TB,H](MeAcry)(O)}$_2$ (seb). As expected the most stable conformation is an extended form with a very high molecular length to width ratio which is likely to form high $T_{n \to 1}$ liquid crystal monomers.

A minimum energy conformation of a preferred mesogenic dimer is decanedioic acid bis-(4-{2-tert-butyl-4-[4-(2-methyl-acryloyloxy)-benzoyloxy]-phenoxycarbonyl}-phenyl)ester {CO[H,TB,H](MeAcry)(O)}$_2$ (seb) (Courtesy-B. K. Norling, UTHSCSA):

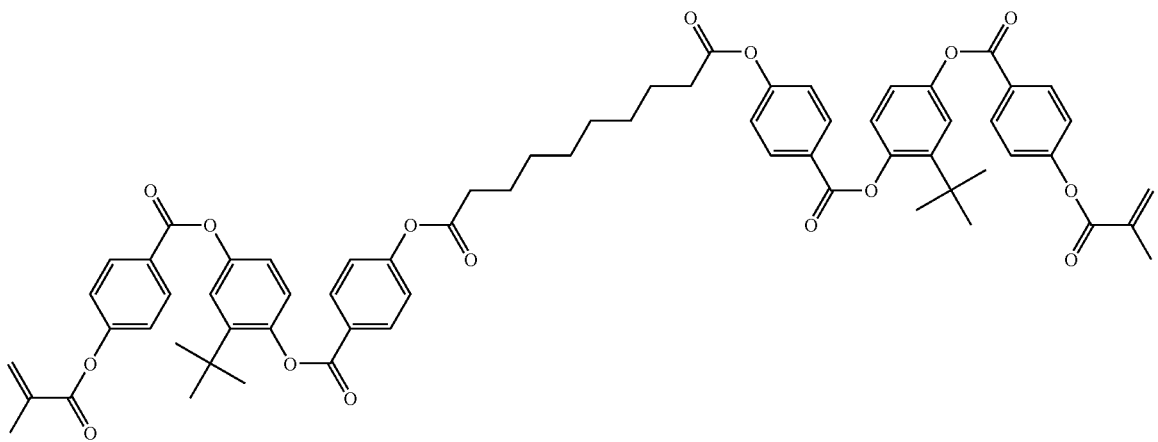

$C_{66}H_{66}O_{16}$
Exact Mass: 1114.44
Mol. Wt.: 1115.22
C, 71.08; H, 5.97; O, 22.95

Alternately, the partially or completely methacryloylated or acryloylated versions of decanedioic acid bis-(4-{2-tert-butyl-4-[4-(hydroxy)-benzoyloxy]-phenoxycarbonyl}-phenyl)ester and decanedioic acid bis-(4-{2-tert-butyl-4-[4-(2-methyl-acryloyloxy)-benzoyloxy]-phenoxycarbonyl}-phenyl)ester are made as illustrated below:
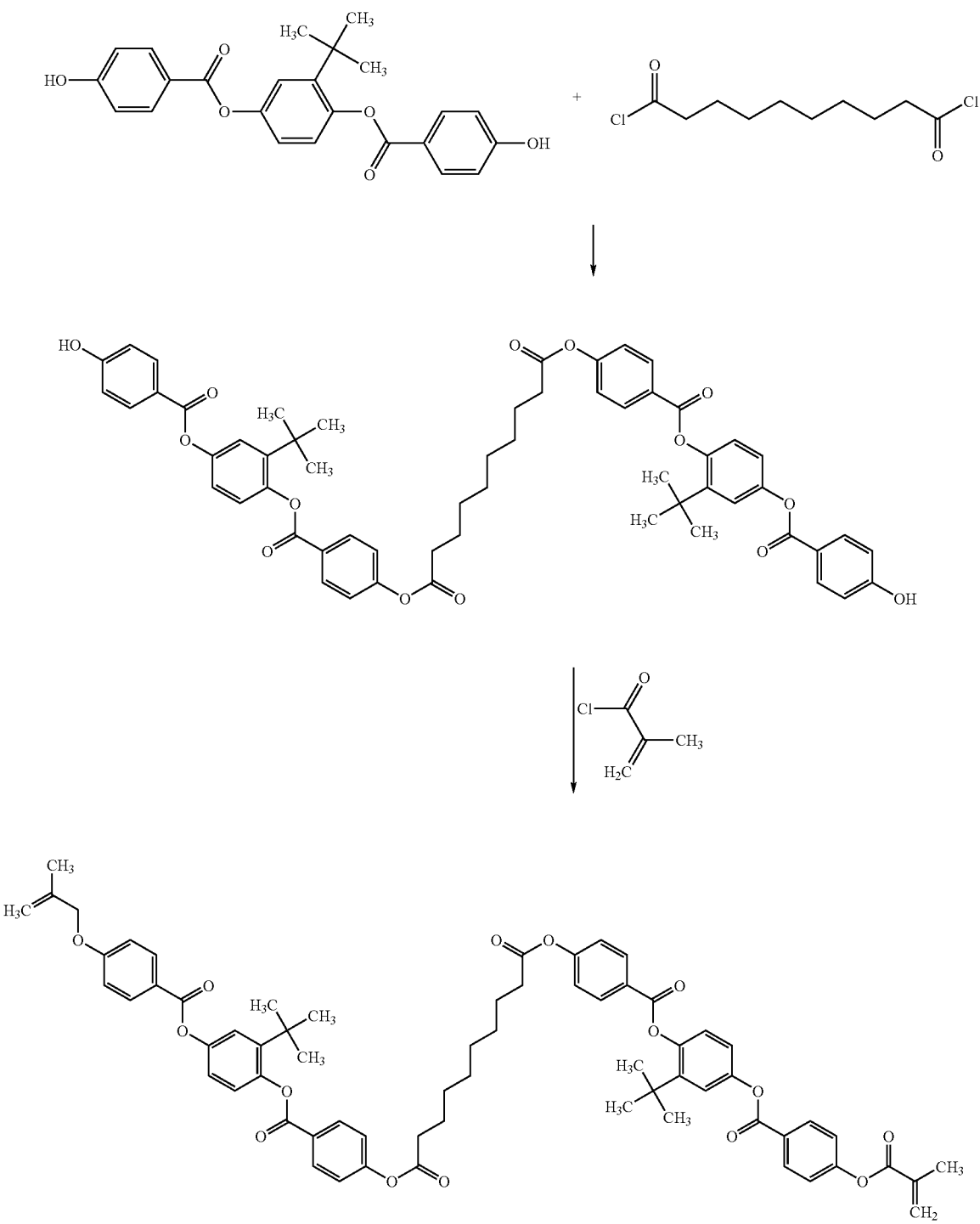

The first reaction product in the above figure is a novel alkylenedioic bis-(4-{2-alkyl-4-[4-(hydroxy)-benzoyloxy]-phenoxycarbonyl}-phenyl)ester having the following general structure:

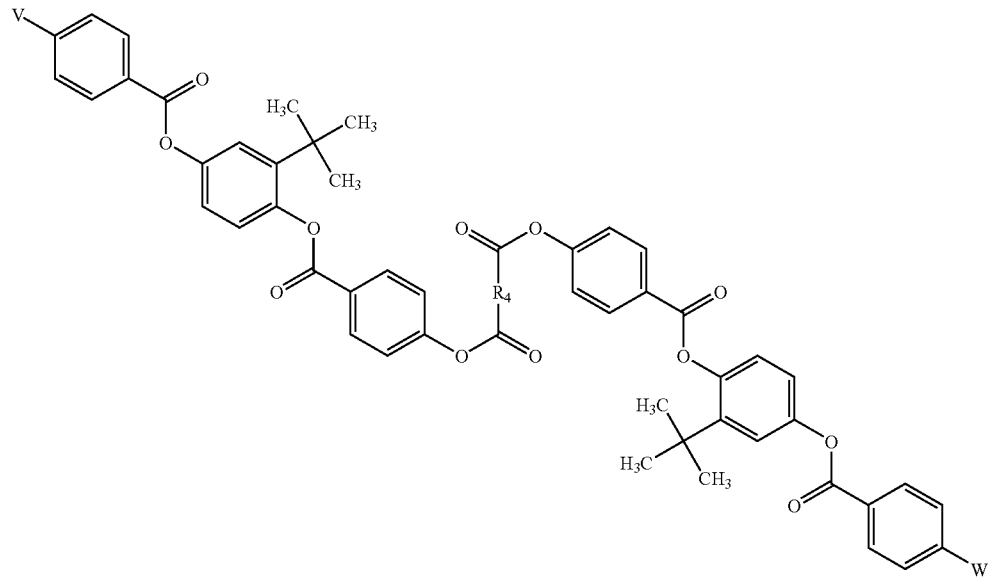

30 wherein
$R^4$ has from about 2 to about 20 carbon atoms, preferably from about 2 to about 12 carbon atoms, and most preferably from about 6 to about 12 carbon atoms.
the alkyl substituent on the central aromatic group of the aromatic ends includes, but is not necessarily limited to methyl groups, t-butyl groups, isopropyl groups, and secondary butyl groups. Most preferred are t-butyl groups; and,
V and W are selected from the group consisting of terminal functionalities and polymerizable groups. In platform molecules, V and W are terminal functionalities. In polymerizable mesogens, V and/or W are polymerizable groups.

Suitable terminal functionalities independently are selected from the group consisting of hydroxyl groups, amino groups, and sulfhydryl groups. Most preferred terminal functionalities are hydroxyl groups.

Suitable polymerizable groups may be polymerized by either free radical polymerization or by nucleophilic addition, and include the groups previously described. Preferred alkenyl esters are acryloyl groups and methacryloyl groups. V and W may be the same or different, depending upon the application. In a preferred application—a dental application—V and W comprises terminal alkenyl groups.

These alkylenedioic bis-(4-{2-alkyl-4-[4-(hydroxy)-benzoyloxy]-phenoxycarbonyl}-phenyl)esters are novel compounds, and may be used as "platform molecules," or polymerizable mesogens. A most preferred alkylenedioic bis-(4-{2-alkyl-4-[4-(hydroxy)-benzoyloxy]-phenoxycarbonyl}-phenyl)ester is decanedioic acid bis-(4-{2-tert-butyl-4-[4-(hydroxy)-benzoyloxy]-phenoxycarbonyl}-phenyl)ester.

In order to make the dihydroxyaromatic terminated mesogens, 1,4 bis(4'-hydroxybenzoyloxy)t-butylphenylene or bis-(4-{2-tert-butyl-4-[4-(hydroxy)-benzoyloxy]-phenoxy carbonyl}-phenyl)ester is dissolved in a solvent at a ratio of about 10 ml. solvent per gram. The material is dissolved in the solvent under an inert gas, preferably dry nitrogen. Suitable solvents are heterocyclic bases, with a preferred solvent being pyridine. This first mixture is diluted with a chlorinated organic solvent, preferably methylene chloride, in an amount equal to the volume of pyridine.

A second mixture is formed by dissolving an alkyloyl chloride in a chlorinated organic solvent at a ratio of about 10 ml solvent per gram of alkyloyl chloride. A preferred chlorinated organic solvent is methylene chloride. The alkyloyl chloride comprises an alkyl portion having from about 2 to about 20 carbon atoms, preferably from about 6 to about 20 carbon atoms, more preferably from about 6 to about 12 carbon atoms, and most preferably is sebacoyl chloride. This second mixture includes at least some of benzoquinone inhibitor, suitable concentrations being from about 1 to about 100 ppm, with a preferred concentration being about 10 ppm. The second mixture is added slowly to the first mixture with stirring, preferably with a syringe through a suba seal. After about 24 hours at room temperature, a precipitate is seen. The solvent, preferably methylene chloride and pyridine, are pumped off.

Any remaining pyridine is converted to a salt using a suitable acid, preferably hydrochloric acid, and the salt is removed by washing with water. Water is filtered off from the remaining white precipitate. Residual water is removed using a suitable solvent, preferably acetone, to dissolve the remaining precipitate, which is then stirred with a suitable amount of magnesium sulfate. The solution is dried down and a dissolved in a chlorinated organic solvent, preferably methylene chloride (DCM), is added to dissolve the solid. After 24 hours at room temperature the unreacted 1,4 bis(4'-hydroxybenoyloxy)t-butylphenylene crystallizes out of solution as a white precipitate and separated from the mixture. The solution was then placed in the freezer overnight and decanedioic acid bis-(4-{2-tert-butyl-4-[4-(hydroxy)-benzoyloxy]-phenoxycarbonyl}-phenyl)ester precipitates out of solution. Silica and basic alumina may be added to absorb any remaining methacrylic acid or carboxylic acid terminated products.

Aromatic terminated mesogens (herein called "mesogenic dimers"), such as the foregoing, are used as a diluent and blended with the aliphatic terminated mesogens (herein called polymerizable mesogen) to form the polymerizable mixture. The quantity of mesogenic dimer in the blend will vary depending upon the dimer and its impact on transition temperature, final product, etc.

Reaction of Dimethyl Amine or Dichloro Terminated Oligodimethylsiloxanes with the Mono Methacrylate ester of 1,4[4'-hydroxybenzoyloxy]t-butylphenylene Molecules with high temperature stability can be prepared by reacting dimethyl amine or dichloro terminated oligodimethylsiloxanes with the mono methacrylate ester of 1,4[4'-hydroxybenzoyloxy]t-butylphenylene, as shown below:

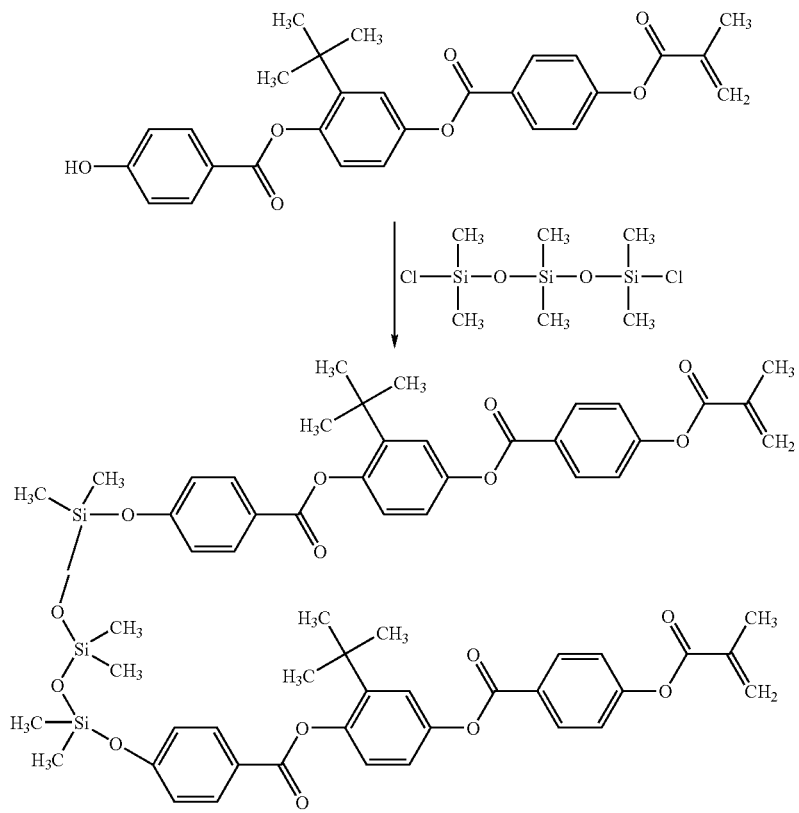

In this, embodiment, the mesogenic platform molecule 1,4[4'-hydroxybenzoyloxy]t-butylphenylene is further extended by reaction with p-anisoyl chloride and subsequent ether methyl group cleavage with aluminum chloride and ethane thiol. Fully aromatic diphenol terminated mesogens of any length can be thus produced. Reaction with acryloyl or methacryloyl chloride forms the monoester, which can be coupled to reactive aliphatic or siloxane oligomers to form polymerizable liquid crystals with reactive ends.

Formation of alkoxy terminal functionalities

In order to produce alkoxy functionalities, an excess of anisoyl chloride is mixed with a desired 1,4 bis(4'-hydroxybenzoyl oxy)-$R^2$ phenylene, (preferably a t-butylphenylene) in an excess of pyridine and triethyl amine (about a 10:1 ratio) with stirring under nitrogen for several hours, preferably about 4 hr. The pyridine is removed under vacuum, and the mixture is extracted into ethyl ether. Amine hydrochloride is removed by vacuum filtration and the remaining solids are washed with a suitable solvent, such as water and acetone. The product had a melting point of 222–224° C. and the structure of the molecule was confirmed by NMR to be the aromatic dimethoxy compound.

Low Polymerization Shrinkage

The mesogens exhibit low polymerization shrinkage. Polymerization shrinkage preferably is measured by first dissolving 0.3 wt. % camphorquinone photoinitiator and 100 ppm benzoquinone together. with 1 wt. % N,N' dimethylaminoethyl methacrylate activator, and then adding the mixture to the monomers. The monomers are then polymerized in film or droplet form in less than 1 minute by exposure to a dental curing light (Dentsply Spectrum Curing Lamp) with a significant output at 420 nm.

FTIR spectroscopy (Nicolet Magna-IR 560) is used to measure the degree of cure by observing the decrease in the 1637 $cm^{-1}$ alkene band vs. the aromatic internal thickness band at 1603 $cm^{-1}$. Thin film measurements that avoid oxygen inhibition are performed by sandwiching the monomer between polyvinylidene chloride films, which have an optical window in the wavelength region of interest. The IR spectrum of solid droplets is evaluated using a single bounce reflectance measurement. The flat bottom surface of the droplet is pressed against the germanium lense of a Spectra Tech Thunderdome attachment.

Polymerization of the monomers can be observed between transparent polyvinylidene chloride films under cross-polarized optical microscopy in the heated stage of a Nikon Optimat microscope. Little change in the local birefringence and thus local orientation is noted upon polymerization at room temperature or upon heating to 180° C.

Viscosity

The desired viscosity of the resin or resin blend will vary depending upon the application and whether additional materials will be added to the blend. For example, the desired viscosity will be lower where a filler is added. For dental applications, a filler is added, and preferred viscosities at from about 20° C. to about 40° C. are from about 50 to about 100 Poise, based on a targeted final composition with about 80% filler loading.

Fracture Toughness

Compact tension samples (ASTM E399) with known edge crack length are fabricated by photocuring monomer with initiator and activator in silicone molds. After polishing the surface with 600 grit polishing agent and soaking in physiologic saline at 37° C. for 24 hours the samples are tested at room temperature under displacement control at 1 mm/min until failure.

The fracture toughness of the crosslinked, amorphous glass is as high as possible, suitably 0.4 Mpa-m$^{1/2}$ or higher, preferably 0.5 MPa-m$^{1/2}$ or higher, which is the same as that found for photocured, isotropic dimethacrylate based resins such as GTE resin (3M company).

Fillers

Considerable amounts of soluble impurity can be added to the polymerizable mesogens, or a mixture comprising the polymerizable mesogens, without changing the $T_{nematic \rightarrow isotropic}$ transition temperature of the polymerizable mesogens. Thus, a high volume fraction of filler can be added to the polymerizable mesogens and still form a composite that maintains desirable, low viscosity flow and low polymerization shrinkage characteristics at temperatures of curing. Commercial products add up to about 70–80 wt % filler. A preferred embodiment uses about 30 wt. % filler.

A variety of fillers may be used. A preferred filler is amphoteric nano-sized metal oxide particles having a diameter in nanometers which is sufficiently small to provide transparency effective for photopolymerization but sufficiently large to provide effective fracture toughness after photopolymerization. Substantially any "metal" capable of forming an amphoteric metal oxide may be used to form the metal oxide particles. Suitable metallic elements include, but are not necessarily limited to niobium, indium, titanium, zinc, zirconium, tin, cerium, hafnium, tantalum, tungsten, and bismuth. Also suitable in place of the metal in the oxide is the semi-metallic compound, silicon. As used herein, unless otherwise indicated, the term "metal oxide" is defined to include silicon, and the word "metal," when used to refer to the metal oxide is intended to also refer to silicon.

The metal oxides may be made of a single metal, or may be a combination of metals, alone or combined with other impurities or "alloying" elements, including, but not necessarily limited to aluminum, phosphorus, gallium, germanium, barium, strontium, yttrium, antimony, and cesium.

A monomeric liquid crystal (LC) containing a high volume fraction of filler nanoparticles is a highly constrained system. As a result, at least for some monomeric species, both smectic and crystalline transitions should be suppressed. The consequent widening of the stability range of nematic mesophase should permit the composite to polymerize at much lower temperatures than in unfilled systems, resulting in lower polymerization shrinkage.

The metal oxide nanoparticles may be prepared using any known methods, such as "sol-gel" techniques, direct hydrolysis of metal alkoxides by water addition, forced hydrolysis of relatively low-cost metal salts, or non-hydrolytic reactions of metal alkoxides with metal halide salts. Examples of such procedures are shown in the following references, each of which is incorporated herein by reference: W. Stober and A. Fink, J. of Colloid and Interface Science, v. 26, 62–69 (1968); M. Z.-C. Hu, M. T. Harris, and C. H. Byers, J. of Colloid and Interface Science, v. 198, 87–99 (1988); M. Ocafia and E. Matijević, J. of Materials Research, v. 5(5), 1083–1091 (1990); L. Lerot, F. LeGrand, P. de Bruycker, J. of Materials Science, v. 26, 2353–2358 (1991); H. Kumazawa, Y. Hori, and E. Sada, The Chemical Eng'g. Journal, v. 51, 129–133 (1993); S. K. Saha and P. Pramanik, J. of Non-Crystalline Solids, v. 159, 31–37 (1993); M. Andrianainarivelo, R. Corriu, D. Leclercq, P. H. Mutin, and A. Vioux, J. of Materials Chemistry, v. 6(10), 1665–1671 (1996); F. Garbassi, L. Balducci, R. Ungarelli, J. of Non-Crystalline Solids, v. 223, 190–199 (1998); J. Spatz, S. Mössmer, M. Mo[umlaut]ller, M. Kocher, D. Neher, and G. Wegner, Advanced Materials, v. 10(6), 473–475 (1998); R. F. de Farias, and C. Airoldi, J. of Colloid and Interface Science, v. 220, 255–259 (1999); T. J. Trentler, T. E. Denler, J. F. Bertone, A. Agrawal, and V. L. Colvin, J. of the Am. Chemical Soc., v. 121, 1613–1614 (1999); Z. Zhan and H. C. Zheng, J. of Non-Crystalline Solids, v. 243, 26–38 (1999); M. Lade, H. Mays, J. Schmidt, R. Willumeit, and R. Schomäcker, Colloids and Surfaces A: Physiochemical and Eng'g Aspects, v. 163, 3–15 (2000); and the procedure described in "Sol-gel processing with inorganic metal salt precursors," authored by "Michael" Zhong Cheng Hu, licensable via Oak Ridge National Laboratory under ORNL control number ERID 0456.

The application will be better understood with reference to the following examples, which are illustrative only:

EXAMPLE 1

Synthesis of 4-nitrophenylenecarbonyloxy 6'-hexane-1'-ol 60 g 4-nitrobenzoic acid (0.4 mole) was dissolved in 250 ml (2.07 mole) dry hexanediol that had been fused in the reaction vessel at 165° C. 1 ml. tetrabutyltitanate catalyst was added, and the mixture was stirred for 3 hours at 135° C. before cooling to 95° C. where stirring was continued under dynamic vacuum for two days to remove the water of condensation.

The solution was extracted with 1 liter diethyl ether, centrifuged or filtered to remove the catalyst, and then washed two times with 500 ml 5% NaHCO$_3$ to remove unreacted acid and excess diol. After the ether was vacuum evaporated, the residue was dissolved in 150 ml boiling ethanol to which 75 ml water was added. Upon cooling to room temperature bis 1,6-(4 nitrophenylene carbonyloxy) hexane precipitated as 7.61 grams of a yellow powder ($T_m$=112° C.).

The remaining solution was evaporated and redissolved in 150 ml diethyl ether to which was added 75 ml hexane. After crystallization at –20° C. 4-nitrophenylene 4-carbonyloxy 6'-hexane-1'-ol (86.7 grams) was isolated ($T_m$=32–35° C.). NMR indicated that both of these products were greater than 98% purity.

EXAMPLE 2

Synthesis of
4-(6-hydroxyhexyloxy)phenylenecarbonyloxy
6'-hexane 1o-ol 20 ml (0.166 mole) of dry, molten hexanediol was transferred to a flask with an attached short path distillation unit. 200 ml dry dimethylsulfoxide (DMSO) and then 40 ml of 1M KOBu$^t$ was then added to the diol and stirred 45 minutes at room temperature. The Bu$^t$OH and a small amount of DMSO were distilled off under vacuum between 25–50° C. over one hour. 8ml (0.04 mole) of dry 4-nitrophenylenecarbonyloxy 6'-hexane-1'-ol was added producing a bright blue color that converted to a yellow coloration after 2 hours.

After stirring overnight, the DMSO and excess hexanediol was removed by vacuum distillation at 90° C., whereupon the residue was taken up in 200 ml diethyl ether which was washed twice with 200 ml 5% NaHCO$_3$ and dried with MgSO$_4$. After the ether was distilled away, the solid was dissolved in a minimum amount of boiling ethanol and crystallized at –20° C. A 75–90% yield of the desired white product was obtained ($T_m$=30–33° C.).

EXAMPLE 3

Synthesis of 4-[6-hydroxyhexyloxyl Benzoic Acid 1.2 g (0.0037 mole) 4-(6-hydroxyhexyloxy)phenylenecarboxyoxy 6'-hexane 1'-ol was heated for 8 hours at 90° C. in a solution of 0.29 g (0.0074 mole) NaOH in 4 ml water. 20 ml of water was added to the clear solution and 0.3 ml of concentrated HCl added to precipitate the acid at pH=3–5. The white solid was filtered off and dried under vacuum to produce a quantitative yield of the substituted benzoic acid ($T_m$=117° C.).

EXAMPLE 4

Synthesis of 4 (6'-chlorohexyloxy)benzoyl Chloride

A three times molar excess of thionyl chloride (55 ml) in toluene (300 ml) was dropwise added over 20 minutes to 4-(6'-hydroxyhexyloxy)benzoic acid (60 g, 0.252 mole) suspended in toluene (600 ml) with a stoichiometric amount of pyridine (42 ml) at 0° C. The suspension was continuously stirred for another 8 hours at room temperature, whereupon the toluene and excess thionyl chloride were distilled off at 70–100° C. with a slight nitrogen flow. The remaining slush of the pyridine hydrochloride and product was extracted with 11 boiling hexane and mixed with 5 g basic alumina and 5 g neutral silica and filtered hot. A 90% yield of a very light yellow 4-(6'-chlorohexyloxy)benzoyl chloride liquid was obtained after evaporation of the hexane ($T_m$<20° C.).

EXAMPLE 5

Synthesis of bis 1,4[4"-(6'-chlorohexyloxy)benzoyloxy]t-butylphenylene 65 g of 4-(6'-chlorohexyoxy)benzoyl chloride (0.23 mole) was added to 16.75 g (0.1 mole) of t-butyl hydroquinone dissolved in 800 ml dry diethyl ether. 10 ml pyridine and 32 ml triethylamine were then added to this mixture. After stirring for 20 hours, the ether was filtered and washed two times with 200 ml 0.1N HCl and 200 ml saturated NaCl solution. The ether solution was then mixed with 10 g basic alumina to remove unreacted acid and 10 g neutral silica to flocculate the suspension and dried over magnesium sulfate. The product starts to crystallize from the ether when the solution is reduced by half. After continued crystallization at –20° C. overnight 63 g of product melting at 95–100° C. could be obtained. Another crop of crystals was obtained by further reducing the solution and crystallizing at –20° C. over one week. NMR purity was >99%.

EXAMPLE 6

Synthesis of bis 1,4[4"-(6'-iodohexyloxy)benzoyloxy]t-butylphenylene 1.15 g (0.0016 mole) bis 1,4[4"-(6'-chlorohexyloxy)benzoyloxy]t-butylphenylene dissolved in 20 ml acetone was boiled under nitrogen with 8.0 g NaI in 20 ml acetone for 20 hours. A quantitative yield of bis 1,4[4"-(6'-iodohexyloxy)benzoyloxy]t-butylphenylene was obtained. The material melted at 76° C. and was >99% pure by NMR.

EXAMPLE 7

Synthesis of bis 1,4[4"-(6'-hydroxyhexyloxy)benzoyloxy]t-butylphenylene 36 g of bis 1,4[4"-(6'-chlorohexyloxy)benzoyloxy]t-butylphenylene was dissolved in 750 ml of n-methypyrrolidinone (NMP) in a single neck flask. 15 g KBr and 120 ml water were then added. The flask was then wired shut with a suba seal, and the solution was heated to 120° C. for 24 hours. Upon cooling, the solution was quenched into 1500 ml water and extracted with 250 ml methylene chloride. After evaporation of the methylene chloride, the solid was extracted with 11 of ether and washed with 11 water and dried with MgSO$_4$. The solution was concentrated and crystallized at –20° C. for 3 days to yield 17 g of white product melting at 80° C. Additional product crystallized from the solution after several weeks. NMR purity was >99%.

Stopping the above reaction at intermediate times yielded mixtures of di-OH terminated, and asymmetric monochloro, monohydroxy compounds.

EXAMPLE 8

Synthesis of bis 1,4[4"-(6'-methacryloyloxyhexyloxy)benzoyloxy]t-butylphenylene 10 g (0.0165 mole) bis 1,4[4"-(6'-hydroxyhexyloxy)benzoyloxy]t-butylphenylene was dissolved in 200 ml dry methylene chloride containing 100 ppm benzoquinone (free radical quencher). After cooling the above solution to 0° C. 3.2 ml (0.035 mole) distilled methacryloyl chloride was then added along with 3 ml (0.037 mole) pyridine and the solution was stirred for 24 hours in a sealed flask making no attempt to remove air from the solvent.

The solvent was vacuum evaporated and the resultant solid taken up in 250 ml ether and washed with 250 ml 0.1N H Cl and 250 ml saturated NaCl. After drying with MgSO$_4$ and filtering, the solvent was evaporated to yield 10 g of the desired product as a nematic liquid, which was >98% pure by NMR. This material could be crystallized from diethyl ether at –20° C. to form a white crystalline solid melting at 57° C.

EXAMPLE 9

Synthesis of bis 1,4[4"-(6'-cinnamoyloxyhexyloxy) benzoyloxy]t-butylphenylene 5 g (0.0825 mole) of bis 1,4[4"-(6'-hydroxyhexyloxy) benzoyloxy]t-butylphenylene was dissolved in 100 ml dry methylene chloride containing 100 ppm benzoquinone (free radical quencher). After cooling the above solution to 0° C., 3.0 g (0.018 mole) cinnamoyl chloride was then added along with 1.4 ml (0.017 mole) pyridine, and the solution was stirred for 24 hours in a sealed flask making no attempt to remove air from the solvent.

The solvent was vacuum-evaporated and the resultant solid taken up in 100 ml ether and washed with 100 ml 0.1N HCl and 250 ml saturated NaCl. After drying with $MgSO_4$ and filtering, the solvent was evaporated to yield 5 g of the desired product which was >98% pure by NMR. This material could be crystallized from diethyl ether at −20° C. to form a white crystalline solid melting at 70° C.

EXAMPLE 10

Synthesis of bis 1,4[4"-(6'-acetoxyoxyhexyloxy) benzoyloxy]t-butylphenylene 1 g (0.0165 mole) of bis 1,4[4"-(6'-hydroxyhexyloxy) benzoyloxy]t-butylphenylene was dissolved in 20 ml dry methylene chloride. After cooling the above solution to 0° C., 0.27 ml (0.0037 mole) acetyl chloride was then added along with 0.3 ml pyridine, and the solution was stirred for 24 hours in a sealed flask.

The solvent was vacuum-evaporated and the resultant solid taken up in 20 ml ether and washed with 20 ml 0.1N HCl and 250 ml saturated NaCl. After drying with $MgSO_4$ and filtering, the solvent was evaporated to yield the product quantitatively at >98% purity by NMR. This material could be crystallized from diethyl ether at −20° C. to form a white crystalline solid melting at 82° C.

EXAMPLE 11

Synthesis of 1,4 Bis(4'-methoxybenzoyloxy)t-butylphenylene

Anisoyl chloride (4.93 g, 0.029 mole), t-butyl hydroquinone (2.00 g, 0.012 mole) in pyridine (50 ml) and triethyl amine (3.2 ml) were stirred under nitrogen for 4 hours with the mixture eventually becoming dark orange/red. The pyridine was removed under vacuum and the mixture was precipitated into ethyl ether (500 ml). Amine hydrochloride precipitated out of solution and was removed by vacuum filtration. The ether was evaporated and the slightly yellow crystals were dissolved in chloroform and extracted with slightly acidified water. The color of the crystals was then removed by stirring over basic alumina and the crystals were then purified by recrystallization in isopropanol. 4.8 grams of material was collected (88% yield) with a melting point of 138–140° C. The structure of the molecule was confirmed by NMR.

EXAMPLE 12

Synthesis of 1,4 Bis(4'-hydroxybenzoyloxy)t-butylphenylene 1,4 Bis(4-methoxybenzoyloxy)t-butylphenylene (0.5 g., 0.00115 mole) and aluminum chloride (1.23 g., 0.00921 mole) were added to ethane thiol (2.5 ml) and dichloromethane (2.5 ml) to form a slightly yellow solution. This mixture was stirred for 1 hour and a white solid precipitated out of solution during this time. The mixture was precipitated into 200 ml of water and extracted with ethyl ether. The ether was evaporated and 0.432 grams were recovered, (92% yield). The melting point was not determined, but was found in be in excess of 280° C.

EXAMPLE 13

Synthesis of 1,4 Bis(4"-(4'-methoxybenzoyloxy) benzoyloxy)t-butylphenylene

The dark orange solution of anisoyl chloride (0.357 g, 2.096 mmole), 1,4 bis(4'-methoxybenzoyloxy)t-butylphenylene (0.355 g, 0.873 mmole) in pyridine (25 ml) and triethyl amine (0.5 ml) were stirred under nitrogen for 4 hr. The pyridine was removed under vacuum, and the mixture was extracted into ethyl ether (200 ml). Amine hydrochloride and the product were insoluble and were removed by vacuum filtration. The amine hydrochloride was removed by washing the solids with water and acetone. The product had a melting point of 222–224° C. and the structure of the molecule was confirmed by NMR.

EXAMPLE 14

Synthesis of bis-(4-{2-tert-butyl-4-[4-(2-methyl-acryloyloxy)-benzoyloxy]-phenoxycarbonyl}-phenyl)ester{CO[H,TB,H](MeAcry)(O)}$_2$ In order to make decanedioic acid bis-(4-{2-tert-butyl-4-[4-(2-methyl-acryloyloxy)-benzoyloxy]-phenoxycarbonyl}-phenyl)ester{CO[H,TB,H](MeAcry)(O)}$_2$ (seb), 0.95 g, 1.95 mmole of 1-(hydroxybenzoyloxy),4-(4'-methacryloyl-benzoyloxy)t-butylphenylene was dissolved in 10 ml dry pyridine under dry nitrogen and then diluted with 20 ml dry methylene chloride. 0.233 g sebacoyl chloride (0.975 mmol) was dissolved in 10 ml dry methylene chloride containing 10 ppm benzoquinone inhibitor and added slowly with syringe through a suba seal into the first solution with stirring. After 29 hours at room temperature a small amount of precipitate was seen and the methylene chloride was pumped off and 0.01 g paradimethylaminopyridine was added as a catalyst to continue the reaction.

After another 24 hours at room temperature, some unconverted phenol was still observed by TLC and 0.5 ml methacryloyl chloride was dissolved in 10 ml dry methylene chloride and added to the reaction mixture to react any unconverted starting material to the dimethacrylate. After 3 hours the phenol had been completely converted and methylene chloride was removed under vacuum.

100 ml of water containing 7.5 ml concentrated HCl was added to the flask with stirring and stirred for four hours to remove the pyridine as the hydrochloride salt (pH=4). The water layer could be poured from the white layer which stuck to the walls of the vessel. After washing once more with deionized water, 100 ml methylene chloride was added to dissolve the solid and the resulting organic phase was transferred to a separatory funnel and washed twice with 100 ml brine saturated water and dried with magnesium sulfate. One gram each of silica and basic alumina were added to absorb any remaining methacrylic acid or carboxylic acid terminated products.

After standing for 8 hours the methylene chloride solution was filtered and added to 500 ml of stirred hexane. After 8 hours the pure precipitated product was collected; the supernatant contained methacrylated starting material.

The white precipitate eluted in 80/20 ether/hexane on silica as a major spot and a very faint following spot. NMR revealed about 95% purity of the desired product (30% yield) with the rest being a methoxy terminated product which was carried over from the diphenol starting material. Solutions could be cast into a translucent, nematic glass at room temperature which gradually softened upon heating.

EXAMPLE 15

Synthesis of bis-(4-{2-tert-butyl-4-[4-(2-methyl-acryloyloxy)-benzoyloxy]-phenoxycarbonyl}-phenyl)ester{CO]H,TB,H](MeAcry)(O)}$_2$ In order to make decanedioic acid bis-(4-{2-tert-butyl-4-[4-(2-methyl-acryloyloxy)-benzoyloxy]-phenoxycarbonyl}-phenyl)ester{CO[H,TB,H](MeAcry)(O)}$_2$ (seb), 0.95 g, 1.95mmole of 1-(hydroxybenzoyloxy),4-(4'-methacryloyl-benzoyloxy)t-butylphenylene was dissolved in 10 ml dry pyridine under dry nitrogen and then diluted with 20 ml dry methylene chloride. 0.233 g sebacoyl chloride (0.975 mmol) was dissolved in 10 ml dry methylene chloride containing 10 ppm benzoquinone inhibitor and added slowly with syringe through a suba seal into the first solution with stirring. After 29 hours at room temperature a small amount of precipitate was seen and the methylene chloride was pumped off and 0.01 g paradimethylaminopyridine was added as a catalyst to continue the reaction.

After another 24 hours at room temperature, some unconverted phenol was still observed by TLC and 0.5 ml methacryloyl chloride was dissolved in 10 ml dry methylene chloride and added to the reaction mixture to react any unconverted starting material to the dimethacrylate. After 3 hours the phenol had been completely converted and methylene chloride was removed under vacuum.

100 ml of water containing 7.5 ml concentrated HCl was added to the flask with stirring and stirred for four hours to remove the pyridine as the hydrochloride salt (pH=4). The water layer could be poured from the white layer which stuck to the walls of the vessel. After washing once more with deionized water, 100 ml methylene chloride was added to dissolve the solid and the resulting organic phase was transferred to a separatory funnel and washed twice with 100 ml brine saturated water and dried with magnesium sulfate. One gram each of silica and basic alumina were added to absorb any remaining methacrylic acid or carboxylic acid terminated products.

After standing for 8 hours the methylene chloride solution was filtered and added to 500 ml of stirred hexane. After 8 hours the pure precipitated product was collected; the supernatant contained methacrylated starting material.

The white precipitate eluted in 80/20 ether/hexane on silica as a major spot 20 and a very faint following spot. NMR revealed about 95% purity of the desired product (30% yield) with the rest being a methoxy terminated product which was carried over from the diphenol starting material. Solutions could be cast into a translucent, nematic glass at room temperature which gradually softened upon heating.

EXAMPLE 16

Synthesis of Decanedioic Acid bis-(4-{2-tert-butyl-4-[4-(hydroxy)-benzoyloxy]-phenoxycarbonyl}-phenyl)ester 18.25 g, (44.9 mmole) of 1,4 bis(4'-hydroxybenzoyloxy) t-butylphenylene was dissolved in 120 ml dry pyridine under dry nitrogen and then diluted with 100 ml dry methylene chloride. 1.34 g sebacoyl chloride (5.60 mmol) was dissolved in 20 ml dry methylene chloride and added slowly with syringe through a suba seal into the first solution with stirring. After 24 hours at room temperature a small amount of precipitate was seen and the methylene chloride and pyridine were pumped off 300 ml of water containing 7.5 ml concentrated HCl was added to the flask with stirring and stirred for four hours to remove the pyridine as the hydrochloride salt (pH=4). The water was filtered off from the white precipitate that formed in the vessel. 200 ml of acetone was added to dissolve the mixture which was then stirred with 3 grams of magnesium sulfate to remove any remaining water, after which the solution was dried down. 200 ml methylene chloride (DCM) was added to dissolve the solid. After 24 hours at room temperature the unreacted 1,4 bis(4'-hydroxybenoyloxy)t-butylphenylene crystallized out of solution as a white precipitate. The solution was then placed in the freezer overnight and decanedioic acid bis-(4-{2-tert-butyl-4-[4-(hydroxy)-benzoyloxy]-phenoxycarbonyl}-phenyl)ester precipitated out of solution.

The white precipitate eluted in 90/10 DCM/acetone on silica as a major spot and a very faint spots resulting from higher order polymerization. The product had a high NMR purity (>95%).

EXAMPLE 17

Synthesis of Decanedioic Acid bis-(4-{2-tert-butyl-4-[4-(2-methyl-acryloyloxy)-benzoyloxy]-phenoxycarbonyl]-phenyl)ester 0.85 g, (0.868 mmole) of decanedioic acid bis-(4-{2-tert-butyl-4-[4-(hydroxy)-benzoyloxy]-phenoxycarbonyl}-phenyl)ester was dissolved in 20 ml dry pyridine under dry nitrogen and then diluted with 20 ml dry methylene chloride. 0.118 g methacrylol chloride (1.13 mmol) was dissolved in 10 ml dry methylene chloride containing 10 ppm benzoquinone inhibitor and added slowly with syringe through a suba seal into the first solution with stirring. After 24 hours at room temperature a small amount of precipitate was seen and the methylene chloride and pyridine were pumped off.

100 ml of water containing 1.0 ml concentrated HCl was added to the flask with stirring and stirred for two hours to remove the pyridine as the hydrochloride salt (pH=4). The water layer could be poured from the white layer, which stuck to the walls of the vessel. After washing once more with deionized water, 50 ml methylene chloride was added to dissolve the solid and the resulting organic phase was transferred to a separatory funnel and washed twice with 100 ml brine saturated water and dried with magnesium sulfate. One gram each of silica and basic alumina were added to absorb any remaining methacrylic acid or carboxylic acid terminated products. NMR revealed that the product was the desired dialkene terminated monomer.

EXAMPLE 18

Synthesis of oligo {[α,ω-diadipoyl]-co-[(bis-1,4-oxybenzoyloxy)-1',4'-(2'-t-butyl-phenylene)]-terminal-{oxyethylmethacrylate}$_2$[C(H,TB,H)$_x$(adipoyl)$_y$ (HEMA)$_z$]

97.22 g (0.3382 mole) of tribenzylamine was dissolved in 1 L of dry methylene chloride in a two-liter flask. 44.02 g (0.3382 mole) of hydroxyethyl methacrylate and 41.27 g (0.2255 mole) of adipoyl chloride were added to the flask and stirred under nitrogen for 6 hours. 22.91 g (0.0564 mole)of 1,4 Bis(4'-hydroxybenzoyloxy)t-butylphenylene and 8.92 g (0.1127 mole) of pyridine were added to the flask and stirred under nitrogen for an additional 12 hours.

The solvent was vacuum-evaporated and the material taken up into 500 ml of ethyl ether. The amine hydrochloride salts precipitated out of the ether and were filtered off; oligomers higher than dimer were relatively insoluble in diethyl ether. The ethyl ether was then vacuum-evaporated. The material was extracted twice with 200 ml of isopropanol and the remaining solids consisted of approximately 77wt % monomer and 23wt % dimer with a trace amount of trimer (Mixture A). Mixture A exhibited $T_{n \rightarrow n+1} = 43°$ C. and $T_{n+1 \rightarrow I}$ of 60° C. and a viscosity of 2000 P at 25° C.

Mixture A was further separated into monomer ($M_a$) and dimer ($D_a$) by extracting Mixture A with a large quantity of methanol in which $M_a$ was soluble. $M_a$ was a clear fluid with a viscosity of 20 P at RT while $D_a$ had a sharp, reversible $T_{n \rightarrow 1} = 100°$ C. and was a viscous, sticky white fluid. Table 1 shows the approximate phase diagram of mixtures of $M_a$ and $D_a$.

TABLE 1

Phase Diagram of $M_a$ and $D_a$

| Wt % $M_a$ | Wt % $D_a$ | $T_{n \rightarrow n+I}$ | $T_{n \rightarrow I}$ | $T_{n+I \rightarrow I}$ |
|---|---|---|---|---|
| 100 | 0 |  | <20 |  |
| 84 | 16 | <0 |  | 35 |
| 68 | 32 | 25 |  | 60 |
| 49 | 51 | 45 |  | 75 |
| 35 | 65 | 65 |  |  |
| 0 | 100 |  | 100 |  |

In other words, the monomer did not exhibit liquid crystal characteristics, but the dimer did.

Increasing the wt % of the monomer in a mixture—whether of the mixture comprises the dimer, another liquid crystal monomer, or a mixture thereof, generally reduces the $T_{n+1 \rightarrow 1}$ temperature of the mixture. Increasing the wt % of the dimer in a mixture—whether the mixture comprises the monomer or one or more other diluents, generally increases the $T_{n+1 \rightarrow 1}$ temperature of a mixture. Also, given the information in Table 1, the dimer may be mixed with other liquid crystal monomers to more precisely control the rheology of the mixture.

EXAMPLE 19

Synthesis of oligo{[α,ω-disebacoyl]-co-[(bis-1,4-oxybenzoyloxy)-1',4'-(2'-t-butyl-phenylene)]-terminal-{oxyethylmethacrylate}$_2$[C(H,TB,H)$_x$(sebacoyl)$_y$ (HEMA)$_z$]

28.51 g (0.0992 mole) of tribenzylamine was dissolved in 1 L of dry methylene chloride in a two-liter flask. 12.91 g (0.0992 mole) of hydroxyethyl methacrylate and 15.81 (0.0661 mole) of sebacoyl chloride were added to the flask and stirred under nitrogen for 6 hours. 6.72 g (0.0165 mole)of 1,4 Bis(4'-hydroxybenzoyloxy)t-butylphenylene and 2.62 g (0.0331 mole) of pyridine were added to the flask and stirred under nitrogen for an additional 12 hours.

The solvent was vacuum-evaporated and the material taken up into 500 ml of ethyl ether. The amine hydrochloride salts precipitated out of the ether and were filtered off. The ethyl ether was then vacuum-evaporated. The remaining material was a mixture of monomer, dimer, trimer and sebacoyl dimethacrylate. The sebacoyl dimethacrylate was extracted by continuous extraction with 1 liter of hexane for 12 hours. The remaining material was a 4/1 mixture of monomer and dimer with a trace amount of trimer.

Methanol extraction of the mixture yielded the pure monomer, a low viscosity clear fluid with $T_{N \rightarrow 1} = 6°$ C. The remaining thick, white fluid dimer showed $T_{N \rightarrow 1} = 65-70°$ C.

Also of interest was the observation that mixtures of the oligomer blend of Example 2 did not crystallize in the presence of >50wt % of a commercial, Ba glass dental filler at RT over a period of two months.

EXAMPLE 20

Synthesis of oligo {[α,ω-disebacoyl]-co-[(bis-1,4-oxybenzoyloxy)-1',4'-(2'-t-butyl-phenylene)]-terminal-{oxypropylmethacrylate}$_2$[C(H,TB,H)$_x$(sebacoyl)$_y$(HPMA)$_z$]

71.40 g (0.3000 mole) of sebacoyl chloride was dissolved in 500 ml of dry methylene chloride in a one-liter flask. 8.13 g (0.0200 mole) of 1,4 bis(4'-hydroxybenzoyloxy)t-butylphenylene and 3.16 g (0.0400 mole) of pyridine were added to the flask and stirred under nitrogen for 6 hours.

The solvent was vacuum-evaporated and the material taken up into 500 ml of hexane to extract out the excess sebacoyl chloride. The remaining material was dissolved in 500 ml of dry methylene chloride. 15.61 g (0.1200 mole) of hydroxypropyl methacrylate and 18.91 g (0.1200 mole) of pyridine were added to the flask and stirred to 6 hours under nitrogen.

The solvent was vacuum-evaporated and the material taken up into 500 ml of ethyl ether. The amine hydrochloride salts precipitated out of the ether and were filtered off. The ethyl ether layer was stirred 5 times with 10 g with basic alumina to remove sebacic acid end groups. The remaining material was found to be 10/1 monomer to dimer that consisted of entirely primary HPMA addition.

Methanol extraction of the mixture yielded the pure monomer, a low viscosity clear fluid with $T_{n \rightarrow 1} = 16°$ C. The remaining thick, white fluid dimer showed $T_{n \rightarrow 1} = 81-83°$ C.

EXAMPLE 21

Polymerization Shrinkage and Mechanical Properties of Polymerized Liquid Crystal Oligomers Produced in Examples 18–20

The designated liquid crystal monomers were prepared for polymerization by codissolving the oligomer mixture with a solution of 0.3 wt. % camphorquinone photoinitiator, 100 ppm benzoquinone and 1 wt. % N,N'-dimethylamino ethylmethacrylate activator under yellow light. The dialkene terminated oligomers were then polymerized in film, bar or droplet form in 1–10 minutes by exposure to a dental curing light (Dentsply Spectrum Curing Lamp) or a light box with a significant output at 420 nm.

FTIR spectroscopy (Nicolet Magna-IR 560) was utilized to measure the degree of cure by observing the decrease in the 1637 cm$^{-1}$ alkene band vs. the aromatic internal thickness band at 1603 cm$^{-1}$. The IR spectrum of solid droplets was evaluated utilizing a single bounce reflectance measurement. The flat bottom surface of the droplet was pressed against the germanium lense of a Spectra Tech Thunderdome attachment.

Polymerization of the oligomers could be observed between transparent polyvinylidene chloride films under cross-polarized optical microscopy in the heated stage of a Nikon Optimat microscope. Little change in the local birefringence and thus local orientation was noted upon polymerization in the nematic phase and heating to 180° C.

For example, Mixture A showed the very low, ultimate polymerization shrinkage at 37° C. of 1.9% induced by visible light photoexposure after 90% double bond conversion (by IR). Some of the improved polymerization shrinkage in the liquid crystal oligomer in comparison to an isotropic GTE resin (a commercial mixture of dimethacryl terminated isotropic monomers) originates in the lower concentration of double bonds in the LC material and in the fact that GTE resin polymerizes to slightly lower conversions (70%). The remaining difference lies in the disordering that occurs upon conversion of the monomer nematic state to the polymeric nematic state.

EXAMPLE 22

Fracture Toughness and Four Point Bending Strength of Liquid Crystal Polymers

Compact tension samples (ASTM E399) with known edge crack length were fabricated by photocuring the oligomer mixtures with initiator and activator in silicone molds. After polishing the surface with 600 grit polishing agent and soaking in physiologic saline at 37° C. for 24 hours the samples were tested at room temperature under displacement control at 1 mm/min until failure.

The fracture toughness of the crosslinked, glassy Mixture A was 0.34 MPa-m$^{1/2}$, slightly larger than that found for photocured, isotropic dimethacrylate based resins such as GTE resin, 0.23 MPa-m$^{1/2}$.

The bending strength of the crosslinked, glassy Mixture A was 78 Mpa (elastic modulus=1.34 Gpa), less than that found for photocured, isotropic dimethacrylate based resins such as GTE resin, 150 Mpa (elastic modulus=3.7 Gpa). However, of some interest was the observation of ductile yielding in more than half of the Mixture A samples tested.

EXAMPLE 23

Synthesis of [(H,TB,H (sebacoyl)2(HEMA)2] (Lot 103)

473.02 g (1.6458 mole) of tribenzylamine was dissolved in 3 L of dry methylene chloride in a twelve-liter flask. 214.18 g (1.6458 mole) of hydroxyethyl methacrylate, and 262.38 g (1.0972 mole) of sebacoyl chloride were added to the flask and stirred under nitrogen for 6 hours. 111.5 g (0.2743 mole) of 1,4 Bis(4'-hydroxybenzoyloxy)t-butylphenylene, and 43.39 g (0.5486 mole) of pyridine were added to the flask and stirred under nitrogen for an additional 12 hours.

The solvent was vacuum-evaporated and the material taken up into 1000 ml of ethyl ether. The amine hydrochloride salts precipitated out of the ether and were filtered off. The ethyl ether was then vacuum-evaporated. The material was extracted twice with 500 ml of methanol and twice more with 250 ml of methanol. The resulting liquid crystalline material has a transition temperature of 30° C. from the nematic to isotropic states. The viscosity of this material at 20° C. is 3000 Poise at low shear rates, but shear thins down to 60 Poise at 1000 Hz.

EXAMPLE 24

Synthesis of [(H, M,H)(sebacoyl)2(HEMA)2] (Lot 121)

236.94 g (0.8244 mole) of tribenzylamine was dissolved in 3 L of dry methylene chloride in a twelve-liter flask. 107.3 g (0.8244 mole) of hydroxyethyl methacrylate, and 131.45 g (0.5496 mole) of sebacoyl chloride were added to the flask and stirred under nitrogen for 6 hours. 50.00 g (0.1374 mole) of 1,4 Bis(4'-hydroxybenzoyloxy)methylphenylene, and 21.73 g (0.2748 mole) of pyridine were added to the flask and stirred under nitrogen for an additional 12 hours.

The solvent was vacuum-evaporated and the material taken up into 2000 ml of ethyl ether. The amine hydrochloride salts precipitated out of the ether and were filtered off. The ethyl ether was then vacuum-evaporated. The material was extracted three times with 400 ml of hexane, two times with 300 ml of methanol. The resulting liquid crystalline material has a transition temperature of 62° C. from the nematic to isotropic states and appears to have a higher order smectic transition at 35° C. The viscosity material at 37° C. is 20 Poise. When allowed to sit At room temperature (20° C.), the smectic phase forms over time and the viscosity increases to >10,000 Poise.

To decrease the room temperature viscosity of the (H,M, H)(sebacoyl)2 (HEMA)2] (lot 121) material it is combined with (H,TB,H)(sebacoyl)2(HEMA)2] (lot 103). Several combinations were tested and the nematic to isotropic transition temperature of the mixture follows a linear rule of mixtures based upon the weight fraction of is approximately a linear function between the pure lot 103 and pure lot 121. The point at which The smectic transition occurs below room temperature is 20° C. at 61% lot 103 and 39% of lot 121. This mixture has a nematic to isotropic transition of 42° C. and a viscosity of 550 Poise at 20° C. The mixture has a slight shear rate dependence, with the viscosity dropping to 500 poise at 1000 Hz. The higher shear rate dependence of the pure lot 103 was most likely due to the breakup of the smectic structure.

The photopolymerization volumetric shrinkage was measured at 1.62% with a double bond conversion of >90% as confirmed by FTIR.

HPLC and NMR data were obtained for both lots 103 and 121. In both cases the batches consisted of approximately 80% mole ratio of the monomer and about 20% mole ratio of the dimer. There was a trace amount of trimer indicated by the HPLC.

EXAMPLE 25

Synthesis of [(H,TB/M,H)(adipoyl/sebacoyl)2(HEMA)2] (Lot 133)

600.93 g (2.091 mole) of tribenzylamine was dissolved in 6 L of dry methylene chloride in a twelve-liter flask. 272.10 g (2.091 mole) of hydroxyethyl methacrylate, 102.05 g (0.5576 mole) of adipoyl chloride and 200.00 g (0.8363 mole) of sebacoyl chloride were added to the flask and stirred under nitrogen for 6 hours. 70.82 g (0.1742 mole) of 1,4 Bis(4'-hydroxybenzoyloxy)t-butylphenylene, 63.41 g (0.1742 mole) of 1,4 Bis(4'-hydroxybenzoyloxy)methylphenylene, and 55.13 g (0.6969 mole) of pyridine were added to the flask and stirred under nitrogen for an additional 12 hours.

The solvent was vacuum-evaporated and the material taken up into 2000 ml of ethyl ether. The amine hydrochloride salts precipitated out of the ether and were filtered off. The ethyl ether was then vacuum-evaporated. The material was extracted twice with 500 ml of methanol and three times with 200 ml of methanol. The nematic to isotropic transition temperature of this material is 78° C. and the viscosity at 19° C. was 600 Poise with only very slight shear rate dependence.

The photopolymerization volumetric shrinkage was measured at 0.70% with >90% double bond conversion by FTIR.

HPLC data for this mixture shows 15 separate peaks. There are 8 potential liquid crystalline monomer components of this mixture and over 100 possible dimer components considering all of the possible combinations of the reagents. This combination allows for higher transition temperatures while inhibiting the formation of a smectic phase that would increase the viscosity.

EXAMPLE 26

Synthesis of [(H,TB/M,H)(adipoyl/sebacoyl)2(HEMA)2] (Lot 147)

600.93 g (2.091 mole) of tribenzylamine was dissolved in 6 L of dry methylene chloride in a twelve-liter flask. 272.10 g (2.091 mole) of hydroxyethyl methacrylate, 102.05 g (0.5576 mole) of adipoyl chloride and 200.00 g (0.8363 mole) of sebacoyl chloride were added to the flask and stirred under nitrogen for 6 hours. 70.82 g (0.1742 mole) of 1,4 Bis(4'-hydroxybenzoyloxy)t-butylphenylene, 63.41 g (0.1742 mole) of 1,4 Bis(4'-hydroxybenzoyloxy)methylphenylene, and 55.13 g (0.6969 mole) of pyridine were added to the flask and stirred under nitrogen for an additional 12 hours.

The solvent was vacuum-evaporated and the material taken up into 2000 ml of ethyl ether. The amine hydrochloride salts precipitated out of the ether and were filtered off. The ethyl ether was then vacuum-evaporated. The material was extracted six times with 500 ml of hexane and twice with 1000 ml of isopropanol. The transition temperature of this material from nematic to isotropic is 67° C. The viscosities were measured at several temperatures and are tabulated below. The viscosity shear rate relationship is slightly strain rate softening at lower shear rates but Newtonian at higher shear rates.

| Temperature 19° C. | Viscosity 200 Poise |
|---|---|
| 25 | 120 |
| 30 | 90 |
| 37 | 60 |
| 40 | 40 |
| 45 | 35 |
| 50 | 27 |

The photopolymerization volumetric shrinkage measured at 37° C. is ca. 2.16% with >90% double bond conversion by FTIR.

The lower viscosity higher polymerization shrinkage in this mixture relative to that of lot 133 is due to a less rigorous extraction process. The NMR data for this mixture shows that a higher percentage of dimethacroyl sebacate biproduct that was not extracted out. The exact extraction method combined with variation in the ratios of the reagents can be tuned to produce a mixture that results in a variety of shrinkage or viscosity profiles for a given application.

At 75 wt % filler loading with barium glass filler the mixture showed no crystallization or significant Theological changes after 3 months at 25° C.

Persons of ordinary skill in the art will recognize that many modifications may be made to the present application without departing from the spirit and scope of the present application. The embodiment described herein is meant to be illustrative only and should not be taken as limiting the invention, which is defined in the claims.

We claim:

1. A resin blend comprising:
   one or more primary liquid crystal monomer at a ratio to one or more secondary monomer, said secondary monomer and said ratio being adapted to maintain said resin blend in a nematic liquid crystalline state after addition of inorganic filler at a temperature of 20° C. for about 30 minutes or more, the resin blend having a polymerization shrinkage of 3 vol. % or less,
   the primary liquid crystal monomer having the following general structure:

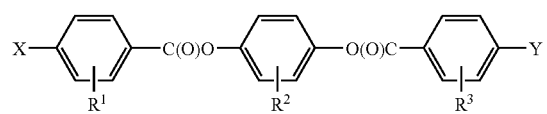

wherein X and Y comprise polymerizable groups;
   $R^2$ is a bulky organic group having a bulk greater than $R_1$ and $R_3$, said bulk being adapted to provide sufficient steric hindrance to achieve a nematic state at room temperature while suppressing crystallinity of liquid crystal monomers made using the mesogens at room temperature; and,
   $R^1$ and $R^3$ are selected from groups less bulky than $R^2$;
   said secondary monomer comprising one or more mesogens having the following general structure:

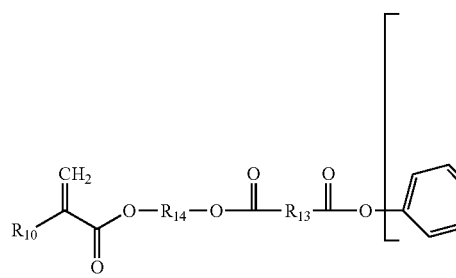 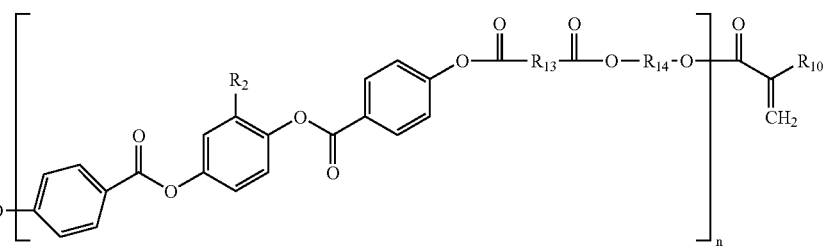

wherein:
n is from about 2 to about 5;
$R^2$ is a bulky organic group;
$R^{10}$ independently is selected from the group consisting of hydrogen and methyl groups;
$R^{14}$ independently is selected from the group consisting of substituted and unsubstituted alkyl groups having from about 2 to about 6 carbon atoms, provided that said substituted alkyl groups consist essentially of one or fewer methyl substituents;
$R^{13}$ independently is selected from the group consisting of alkylene groups having from about 2 to about 12 carbon atoms.

2. The resin blend of claim 1 wherein $R_{14}$ has the following general structure

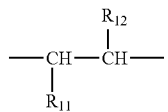

wherein $R^{11}$ and $R^{12}$ independently are selected from the group consisting of hydrogen and methyl groups, provided that no more than one of $R^{11}$ and $R^{12}$ is a methyl group.

3. The resin blend of claim 1 wherein said secondary monomer and said ratio are adapted to maintain said resin blend in a nematic liquid crystalline state after addition of inorganic filler at a temperature of 20° C. for about one month or more.

4. The resin blend of claim 2 wherein said secondary monomer and said ratio are adapted to maintain said resin blend in a nematic liquid crystalline state after addition of inorganic filler at a temperature of 20° C. for about one month or more.

5. The resin blend of claim 1 wherein said secondary monomer and said ratio are adapted to maintain said resin blend in a nematic liquid crystalline state after addition of inorganic filler at a temperature of 20° C. for about 3 months or more.

6. The resin blend of claim 1 having a polymerization shrinkage of 2 vol. % or less.

7. The resin blend of claim 5 having a polymerization shrinkage of 2 vol. % or less.

8. The resin blend of claim 1 having a curing temperature ($T_c$) of from about 20° C. to about 40° C.

9. The resin blend of claim 5 having a curing temperature ($T_c$) of from about 20° C. to about 40° C.

10. The resin blend of claim 7 having a curing temperature ($T_c$) of from about 20° C. to about 40° C.

11. The resin blend of claim 1 comprising substantially equal wt. % of said primary liquid crystal monomer and said secondary monomer.

12. The resin blend of claim 5 comprising substantially equal wt. % of said primary liquid crystal monomer and said secondary monomer.

13. The resin blend of claim 7 comprising substantially equal wt. % of said primary liquid crystal monomer and said secondary monomer.

14. The resin blend of claim 10 comprising substantially equal wt. % of said primary liquid crystal monomer and said secondary monomer.

15. The resin blend of claim 1 wherein $R^2$ is selected from the group consisting of methyl groups, t-butyl groups, isopropyl groups, phenyl groups, and secondary butyl groups.

16. The resin blend of claim 5 wherein $R^2$ is selected from the group consisting of methyl groups, t-butyl groups, isopropyl groups, phenyl groups, and secondary butyl groups.

17. The resin blend of claim 7 wherein $R^2$ is selected from the group consisting of methyl groups, t-butyl groups, isopropyl groups, phenyl groups, and secondary butyl groups.

18. The resin blend of claim 10 wherein $R^2$ is selected from the group consisting of methyl groups, t-butyl groups, isopropyl groups, phenyl groups, and secondary butyl groups.

19. The resin blend of claim 14 wherein $R^2$ is selected from the group consisting of methyl groups, t-butyl groups, isopropyl groups, phenyl groups, and secondary butyl groups.

20. A method for producing a resin blend comprising
producing a mixture comprising a quantity of primary polymerizable mesogen and an amount of one or more secondary polymerizable mesogen selected from the group consisting of mesogenic dimers and polymerizable elongated diphenolic platform molecules comprising four phenylene rings or more, wherein said resin blend has a curing temperature ($T_c$) of about 40° C. or less and, upon curing, exhibits a polymerization shrinkage of about 3 vol % change or less;
said primary polymerizable mesogen having the following general structure:

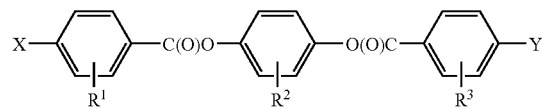

wherein X and Y comprise polymerizable groups;
$R^2$ is a bulky organic group having a bulk greater than $R_1$ and $R_3$, said bulk being adapted to provide sufficient steric hindrance to achieve a nematic state at room temperature while suppressing crystallinity of liquid crystal monomers made using the mesogens at room temperature; and, $R^1$ and $R^3$ are selected from groups less bulky than $R^2$.

21. The method of claim 20 wherein $R^1$ and $R^3$ are selected from the group consisting of hydrogen atoms and methyl groups.

22. The method of claim 20 wherein said primary polymerizable mesogen is bis-(4-(6-methacryloyloxy-A-1-oxy)

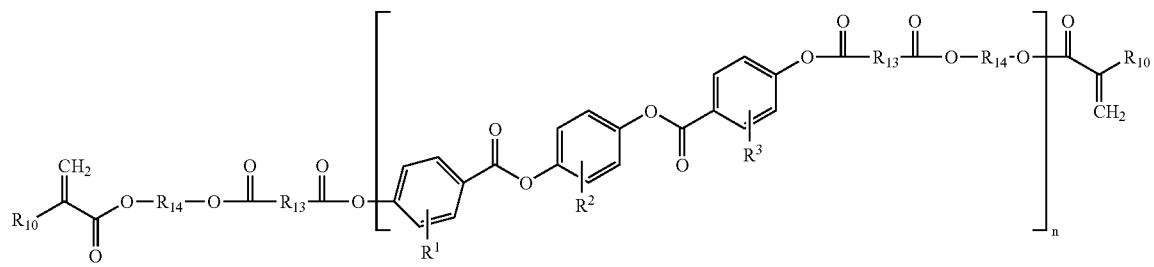

benzoyl)2-(t-butyl)quinone in which A is selected from the group consisting of alkyl groups having from about 2 to about 9 carbon atoms.

23. The method of claim 21 wherein said secondary polymerizable mesogen comprises decanedioic acid bis-(4-{2-tert-butyl-4-[4-(2-methyl-acryloyloxy)-benzoyloxy]-phenoxycarbonyl}-phenyl)ester{CO[H,TB,H](MeAcry)(O)}$_2$ (seb).

24. The method of claim 20 wherein said polymerization shrinkage is about 2 vol % change or less.

25. The method of claim 23 wherein said polymerization shrinkage is about 2 vol % change or less.

26. The method of claim 22 wherein A is a hexyl group.

27. The method of claim 20 wherein said $T_c$ is from about 20° C. to about 40° C.

28. The method of claim 25 wherein said $T_c$ is from about 20° C. to about 40° C.

29. The method of claim 20 wherein $R^2$ is selected from the group consisting of methyl groups, t-butyl groups, isopropyl groups, phenyl groups, and secondary butyl groups.

30. The method of claim 29 wherein $R^2$ is selected from the group consisting of methyl groups, t-butyl groups, isopropyl groups, phenyl groups, and secondary butyl groups.

31. A resin blend comprising:
one or more primary liquid crystal monomer at a ratio to one or more secondary monomer, said secondary monomer and said ratio being adapted to maintain said resin blend in a nematic liquid crystalline state after addition of inorganic filler at a temperature of 20° C. for about 30 minutes or more, the resin blend having a polymerization shrinkage of 3 vol. % or less,
the primary liquid crystal monomer having the following general structure:

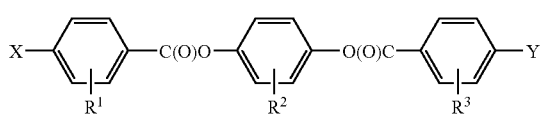

wherein X and Y comprise polymerizable groups;
$R^2$ is a bulky organic group having a bulk greater than $R_1$ and $R_3$, said bulk being adapted to provide sufficient steric hindrance to achieve a nematic state at room temperature while suppressing crystallinity of liquid crystal monomers made using the mesogens at room temperature; and,
$R^1$ and $R^3$ are selected from groups less bulky than $R^2$;
said secondary monomer comprising one or more mesogens having the following general structure:

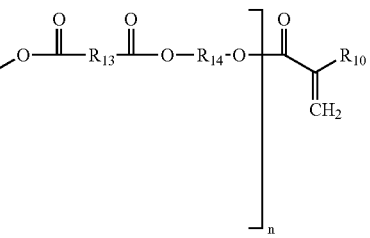

wherein:
n is from about -2 to about 5;
$R^2$ is a bulky organic group;
$R^1$ and $R^3$ are selected from groups less bulky than $R^2$;
$R^{10}$ independently is selected from the group consisting of hydrogen and methyl groups;
$R^{14}$ independently is selected from the group consisting of substituted and unsubstituted alkyl groups having from about 2 to about 6 carbon atoms, provided that said substituted alkyl groups consist essentially of one or fewer methyl substituents;
$R^{13}$ independently is selected from the group consisting of alkylene groups having from about 2 to about 12 carbon atoms.

32. The resin blend of claim 31 wherein $R_{14}$ has the following general structure

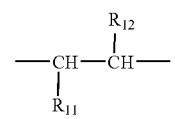

wherein $R^{11}$ and $R^{12}$ independently are selected from the group consisting of hydrogen and methyl groups, provided that no more than one of $R^{11}$ and $R^{12}$ is a methyl group.

33. The resin blend of claim 31 wherein said secondary monomer and said ratio are adapted to maintain said resin blend in a nematic liquid crystalline state after addition of inorganic filler at a temperature of 20° C. for about one month or more.

34. The resin blend of claim 31 wherein said secondary monomer and said ratio are adapted to maintain said resin blend in a nematic liquid crystalline state after addition of inorganic filler at a temperature of 20° C. for about 3 months or more.

35. The resin blend of claim 31 having a polymerization shrinkage of 2 vol. % or less.

36. The resin blend of claim 34 having a polymerization shrinkage of 2 vol. % or less.

37. The resin blend of claim 31 having a curing temperature ($T_c$) of from about 20° C. to about 40° C.

38. The resin blend of claim 34 having a curing temperature ($T_c$) of from about 20° C. to about 40° C.

39. The resin blend of claim 36 having a curing temperature ($T_c$) of from about 20° C. to about 40° C.

40. The resin blend of claim 31 comprising substantially equal wt. % of said primary liquid crystal monomer and said secondary monomer.

41. The resin blend of claim 36 comprising substantially equal wt. % of said primary liquid crystal monomer and said secondary monomer.

42. The resin blend of claim 39 comprising substantially equal wt. % of said first liquid crystal monomer and said secondary monomer.

43. The resin blend of claim 31 wherein $R^2$ is selected from the group consisting of methyl groups, t-butyl groups, isopropyl groups, phenyl groups, and secondary butyl groups.

44. The resin blend of claim 34 wherein $R^2$ is selected from the group consisting of methyl groups, t-butyl groups, isopropyl groups, phenyl groups, and secondary butyl groups.

45. The resin blend of claim 35 wherein $R^2$ is selected from the group consisting of methyl groups, t-butyl groups, isopropyl groups, phenyl groups, and secondary butyl groups.

46. The resin blend of claim 39 wherein $R^2$ is selected from the group consisting of methyl groups, t-butyl groups, isopropyl groups, phenyl groups, and secondary butyl groups.

47. The resin blend of claim 42 wherein $R^2$ is selected from the group consisting of methyl groups, t-butyl groups, isopropyl groups, phenyl groups, and secondary butyl groups.

* * * * *

UNITED STATES PATENT AND TRADEMARK OFFICE
CERTIFICATE OF CORRECTION

| | | |
|---|---|---|
| PATENT NO. | : 7,094,360 B2 | Page 1 of 1 |
| APPLICATION NO. | : 11/010680 | |
| DATED | : August 22, 2006 | |
| INVENTOR(S) | : Wellinghoff et al. | |

It is certified that error appears in the above-identified patent and that said Letters Patent is hereby corrected as shown below:

Column 1, lines 17-18, delete the sentence: "The U.S. government has certain rights in this invention pursuant to grant number NIDCR 1 P01 DE11688." and add the sentence: -- "This invention was made with government support under NIDCR 1 P01 DE11688 awarded by the National Institutes of Health (NIH). The government has certain rights in the invention."--

Signed and Sealed this

Twenty-eighth Day of November, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,094,360 B2 | Page 1 of 1 |
| APPLICATION NO. | : 11/010680 | |
| DATED | : August 22, 2006 | |
| INVENTOR(S) | : Wellinghoff et al. | |

It is certified that error appears in the above-identified patent and that said Letters Patent is hereby corrected as shown below:

In column 43, line 43, in Claim 30, delete "claim 29" and insert -- claim 28 --, therefor.

In column 44, line 24, in Claim 31, delete "about-2" and insert -- about 2 --, therefor.

In column 45, line 12, in Claim 42, delete "first" and insert -- primary --, therefor.

Signed and Sealed this

Twenty-sixth Day of August, 2008

JON W. DUDAS
*Director of the United States Patent and Trademark Office*